(12) United States Patent
Jennings

(10) Patent No.: US 11,726,075 B2
(45) Date of Patent: *Aug. 15, 2023

(54) ADVANCED SYSTEMS AND METHODS FOR MEASURING MUTUAL INDUCTANCE OF AREA OF INFLUENCE

(71) Applicant: FarmX Inc., Mountain View, CA (US)

(72) Inventor: William Eugene Jennings, San Jose, CA (US)

(73) Assignee: FarmX Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/071,507

(22) Filed: Nov. 29, 2022

(65) Prior Publication Data

US 2023/0102531 A1  Mar. 30, 2023

Related U.S. Application Data

(63) Continuation of application No. 17/210,396, filed on Mar. 23, 2021, now Pat. No. 11,519,896, which is a continuation-in-part of application No. 16/994,452, filed on Aug. 14, 2020, now abandoned, which is a continuation of application No. 15/867,594, filed on Jan. 10, 2018, now Pat. No. 10,746,720.

(60) Provisional application No. 62/446,272, filed on Jan. 13, 2017.

(51) Int. Cl.
*G01N 33/24* (2006.01)
*A01G 25/16* (2006.01)
*G01N 27/02* (2006.01)

(52) U.S. Cl.
CPC ......... *G01N 33/246* (2013.01); *A01G 25/167* (2013.01); *G01N 27/025* (2013.01); *G01N 2033/245* (2013.01)

(58) Field of Classification Search
CPC ...... G01N 33/00; G01N 33/24; G01N 33/246; G01N 27/00; G01N 2033/245; A01G 25/00; A01G 25/16; A01G 25/167
USPC .... 324/600, 649, 654, 656, 76.11, 135, 139, 324/436; 239/63
See application file for complete search history.

(56) References Cited

U.S. PATENT DOCUMENTS

2016/0306759 A1* 10/2016 Ham ............... H04L 12/403

FOREIGN PATENT DOCUMENTS

| CN | 202404090 U | * | 8/2012 | ............. G01N 33/24 |
| JP | 2005198560 A | * | 7/2005 | ............. G06F 15/00 |

* cited by examiner

Primary Examiner — Jermele M Hollington
Assistant Examiner — Courtney G McDonnough
(74) Attorney, Agent, or Firm — Carr & Ferrell LLP

(57) ABSTRACT

Soil moisture monitoring systems and methods for measuring mutual inductance of area of influence using radio frequency stimulus are disclosed herein. An example device includes a master element stacked vertically on top of one or more slave elements. The master element and slave elements can communicate through a 1-wire bus configuration. The master element can determine the presence and location of each of the one or more slave elements using an auto-discovery process. The master element can issue commands to the one or more slave elements to obtain moisture readings and/or temperature readings.

20 Claims, 24 Drawing Sheets

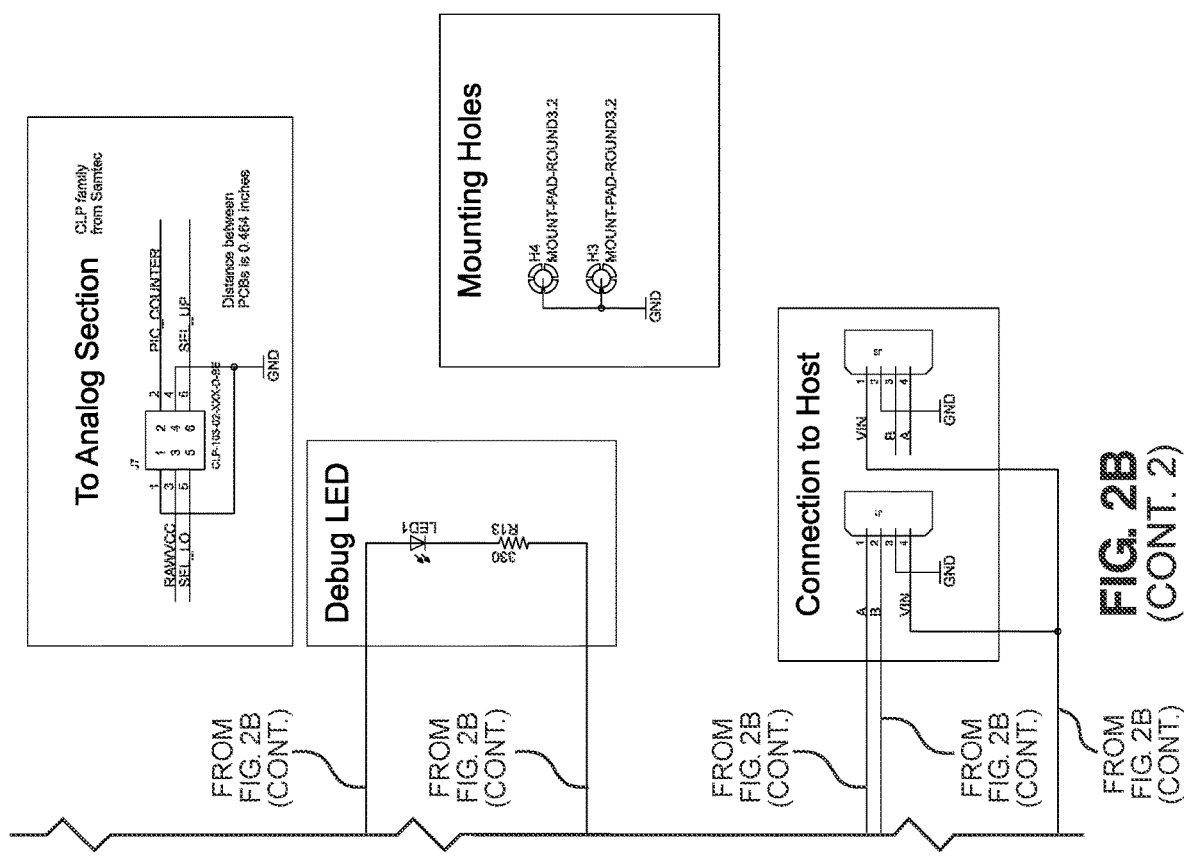

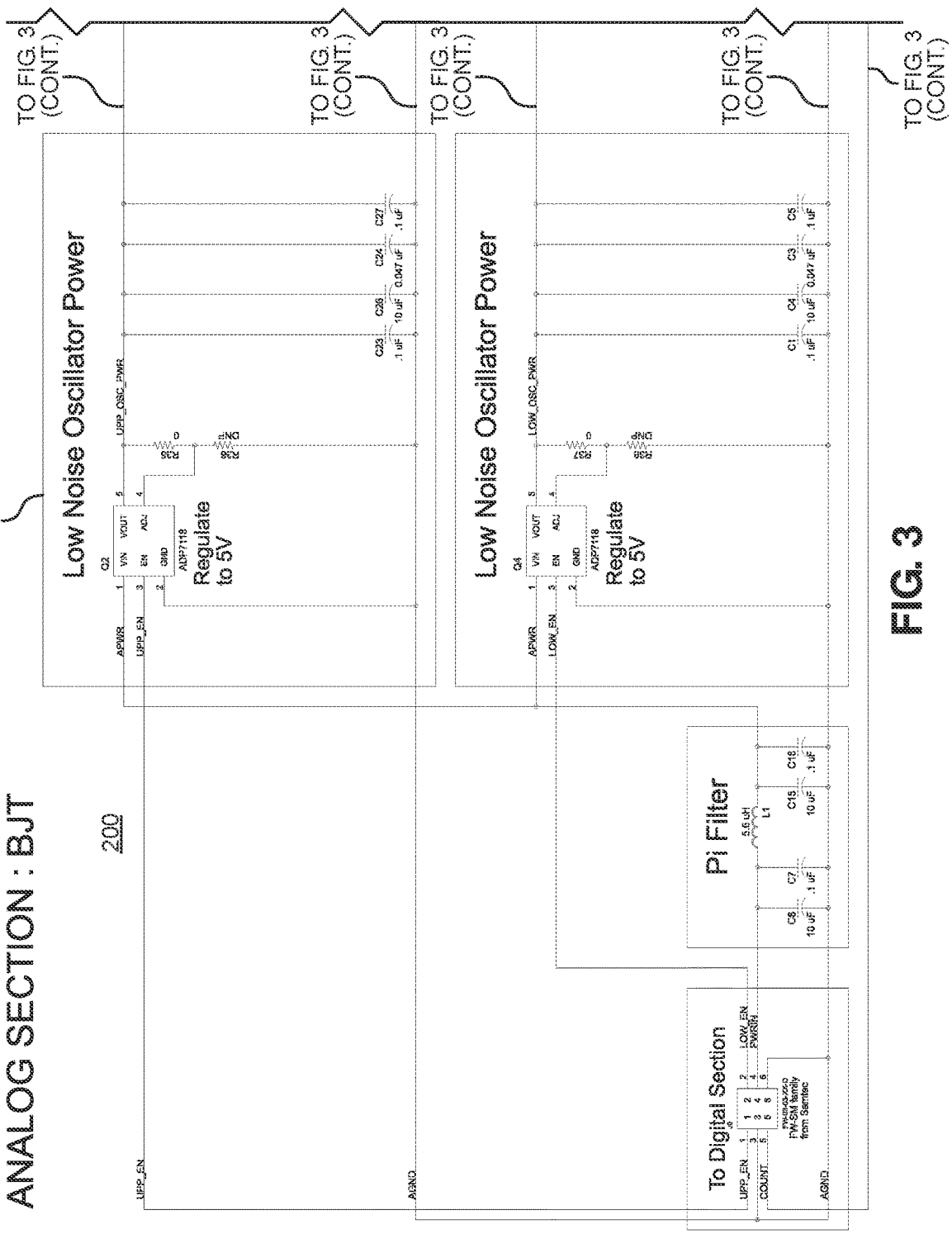

(cont. 2)

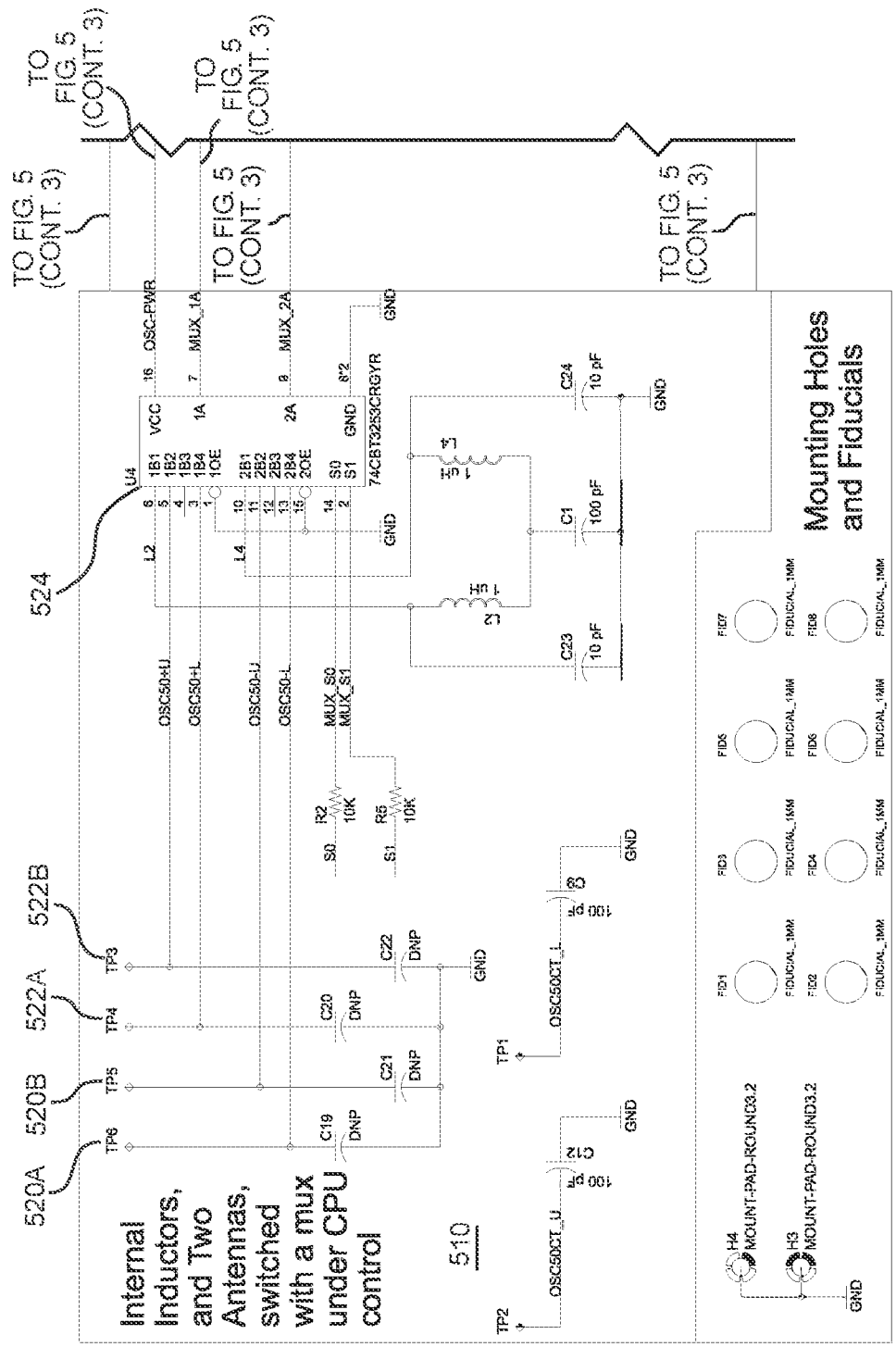
FIG. 5 (cont.2)

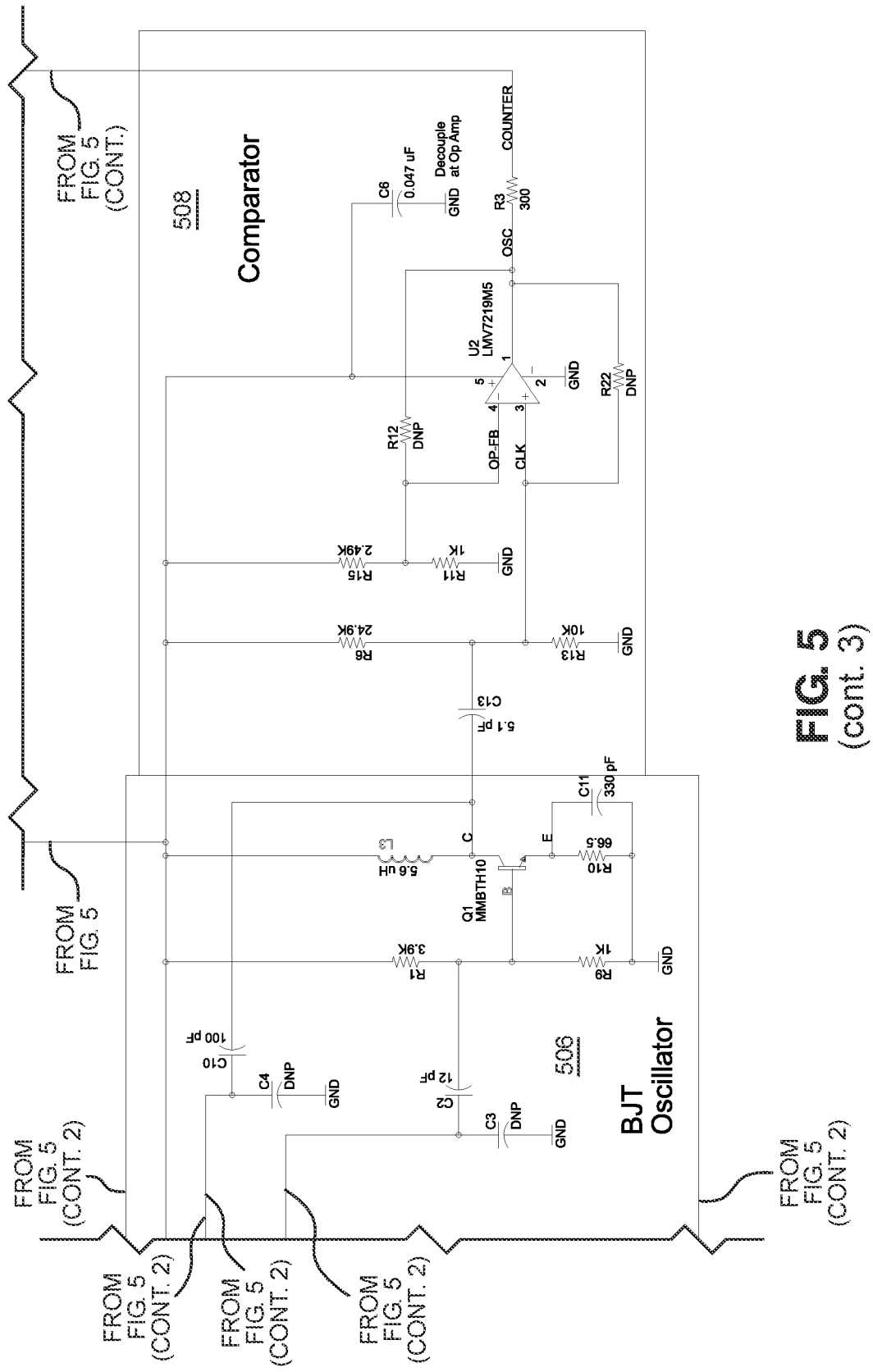
FIG. 5 (cont. 3)

ADVANCED SYSTEMS AND METHODS FOR MEASURING MUTUAL INDUCTANCE OF AREA OF INFLUENCE

CROSS REFERENCE TO RELATED APPLICATION

The present continuation application claims the priority benefit of U.S. Non-Provisional application Ser. No. 17/210,396, filed on Mar. 23, 2021 which is a continuation-in-part of U.S. application Ser. No. 16/994,452, filed on Aug. 14, 2020, which is a continuation of Ser. No. 15/867,594, filed on Jan. 10, 2018, which claims the benefit and priority of U.S. Provisional Application Ser. No. 62/446,272, filed on Jan. 13, 2017, each of which are hereby incorporated by reference including all appendices cited therein, for all purposes.

FIELD OF THE TECHNOLOGY

Embodiments of the disclosure relate to soil moisture monitoring. Some non-limiting embodiments comprise one or more moisture sensor circuits that are placed into the soil at varying depths. The one or more moisture sensor circuits can include a master element and one or more slave elements.

SUMMARY

Embodiments of the present disclosure are directed to device having a housing that encloses: a master element having: a first oscillator and inductor circuit for emitting a first inductance frequency and a second inductance frequency, the first oscillator and inductor circuit being coupled to a first antenna; a CPU (central processing unit) coupled to the first oscillator and inductor circuit; and an analog bus; and a first slave element having: a second oscillator and inductor circuit for emitting a first inductance frequency and a second inductance frequency, the second oscillator and inductor circuit being coupled to a second antenna; a CPU (central processing unit) coupled to the second oscillator and inductor circuit; an upstream analog bus coupled to the analog bus of the master element; and a downstream analog bus configured to couple with another downstream slave element.

Embodiments of the present disclosure are directed to method including waking a master element of a soil analysis device; outputting a first signal or pulse to a first downstream slave element connected to the master element through an analog bus; receiving a response signal or pulse from the first downstream slave element; transmitting a unique identifier downstream to the first downstream slave element; outputting, by the first downstream slave element, a second signal or pulse to a second downstream slave element connected to the first downstream slave element through a downstream analog bus; receiving a response signal or pulse from the second downstream slave element; and transmitting a unique identifier downstream to the second downstream slave element; transmitting, by the master element, a command to either of the first downstream slave element or the second downstream slave element; and receiving a moisture signal and a temperature signal from either of the first downstream slave element or the second downstream slave element based on the command.

Various embodiments of the present disclosure relate to a soil moisture monitor device. In some embodiments the soil moisture monitor device includes: a first oscillator circuit coupled with one or more reference inductors to emit a first inductance frequency; a second oscillator circuit coupled with one or more mutual inductors to emit a first inductance frequency into an area of soil; a microcontroller electrically coupled to the first oscillator circuit and the second oscillator circuit; and a housing positioned within the area of soil, the housing comprising an inner tubular substrate that receives the one or more reference inductors, the one or more mutual inductors, the first oscillator circuit, the second oscillator circuit, and the microcontroller. In some embodiments, the microcontroller is configured to: obtain a first inductance frequency sample using the one or more reference inductors; obtain a second inductance frequency sample using the one or more mutual inductor; obtain a temperature reading from a thermometer; and transmit the first inductance frequency sample, the second inductance frequency sample, and the temperature reading to a receiver.

Various embodiments of the present disclosure relate to a soil moisture monitor method. In some embodiments the soil moisture monitor method includes: receiving a first inductance frequency sample from a first oscillator circuit, the first oscillator circuit being coupled with one or more reference inductors that sense a reference inductance; receiving a second inductance frequency sample from a second oscillator circuit, the second oscillator circuit being coupled with one or more mutual inductors that sense soil moisture inductance in an area of soil. In some embodiments the soil moisture monitor method includes receiving a temperature reading from a thermometer, the temperature reading being obtained when the first inductance frequency sample and the second inductance frequency sample were obtained; and transmitting the first inductance frequency sample, the second inductance frequency sample, and the temperature reading to a receiver.

Various embodiments of the present disclosure relate to a soil moisture monitoring system comprising: a power supply; a time division multiplexer communicatively coupled via a bus to the power supply; a microcontroller communicatively coupled to the time division multiplexer, the microcontroller housed within a housing such as a pvc pipe; an upper oscillator communicatively coupled to the microcontroller, the upper oscillator within the pvc pipe; an upper internal inductor communicatively coupled to the upper oscillator, the upper internal inductor within the pvc pipe; an upper external inductor further comprising an antenna communicatively coupled to the upper oscillator, the upper external inductor and the antenna within the pvc pipe; a lower oscillator communicatively coupled to the microcontroller, the lower oscillator within the pvc pipe; a lower internal inductor communicatively coupled to the lower oscillator, the lower internal inductor within the pvc pipe; a lower external inductor further comprising an antenna communicatively coupled to the lower oscillator, the lower external inductor and the antenna within the pvc pipe; and a thermometer communicatively coupled to the microcontroller, the thermometer within the pvc pipe.

Various embodiments of the present disclosure relate to a soil moisture monitoring method. In some embodiments the soil moisture monitoring method includes: transmitting power to a time division multiplexer; transmitting power from the time division multiplexer to a microcontroller; transmitting identifying information from the microcontroller via a bus to the time division multiplexer; transmitting power from the microcontroller to an oscillator; transmitting power from the oscillator to an internal inductor, the internal inductor not in proximity to soil or soil moisture; transmitting a frequency by the oscillator for a predefined time period as provided by the microcontroller; counting by the internal inductor for the predefined time period a number of reference pulses; turning off the power to the oscillator after the predefined time period; switching a circuit from the internal inductor to an external inductor and antenna in proximity to soil or soil moisture; determining a current soil temperature by a thermometer; turning on the power to the oscillator; waiting for the oscillator to settle; transmitting a frequency by the oscillator for a predefined time period as provided by the microcontroller; counting by the external inductor for the predefined time period a number of soil moisture pulses (inductance of soil); turning off the power to the oscillator; repeating the above steps for a lower second circuit; transmitting for both circuits the reference pulses, the current soil temperatures and the soil moisture pulses via a bus to an external memory; and turning off the power from the time division multiplexer to the microcontroller. Some methods include applying a temperature compensation factor to a difference of the reference pulse and the soil moisture pulse for each circuit in order to determine a volumetric water content. Some methods include temperature compensation factor that is based on the oscillator performance varying with soil temperature. In some embodiments the frequency used by the one or more oscillators is above 30 megahertz.

BRIEF DESCRIPTION OF THE DRAWINGS

While this technology is susceptible of embodiment in many different forms, there is illustrated in the drawings, and will herein be described in detail, several specific embodiments with the understanding that the present disclosure is to be considered as an exemplification of the principles of the technology and is not intended to limit the technology to the embodiments illustrated.

It will be understood that like or analogous elements and/or components, referred to herein, may be identified throughout the drawings with like reference characters. It is further understood that several of the figures are merely schematic representations of the present technology. As such, some of the components may be distorted from their actual scale for pictorial clarity.

DETAILED DESCRIPTION OF EXEMPLARY EMBODIMENTS

Figure 1:
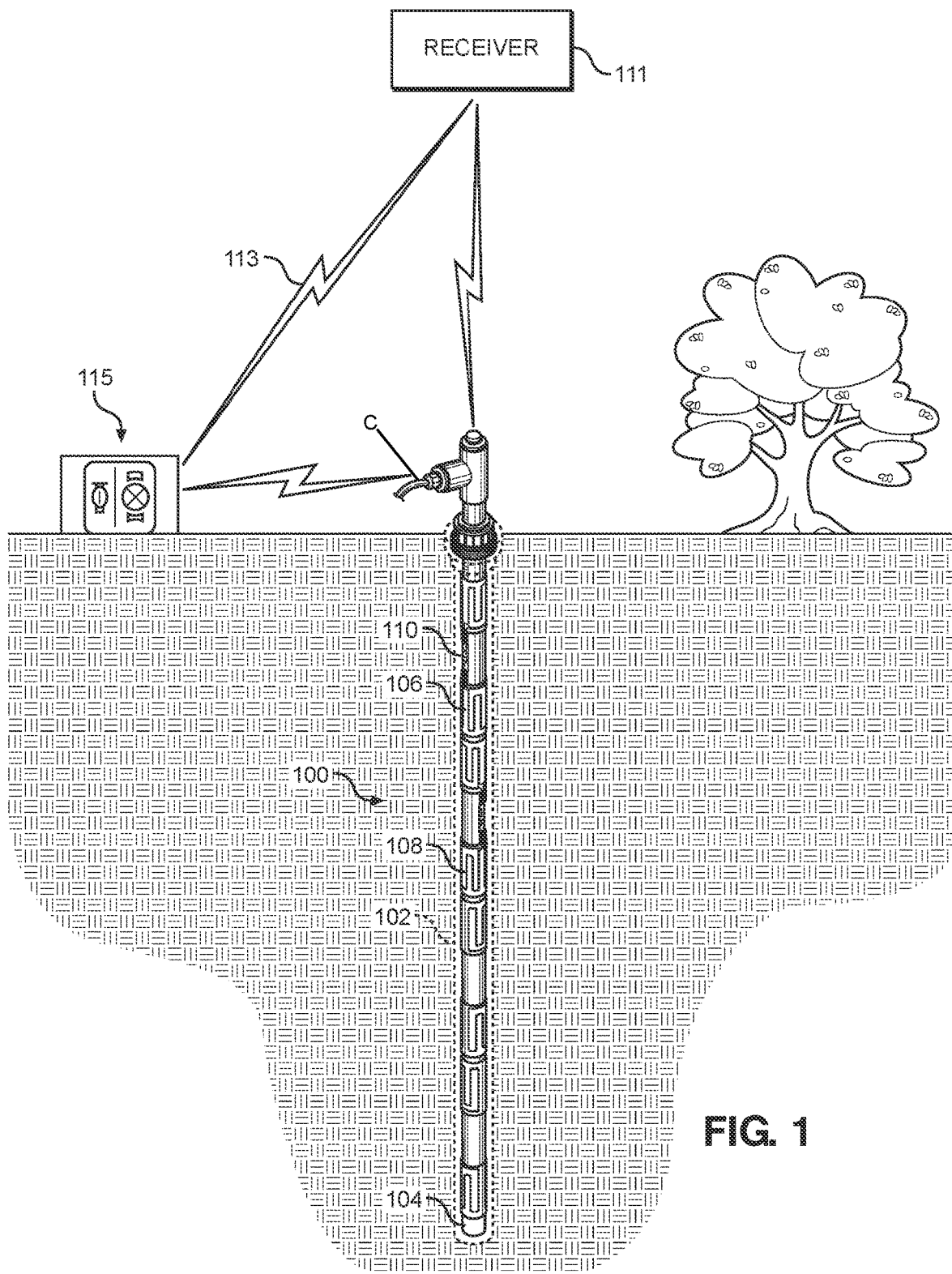
FIG. 1 is a perspective view of an example device that comprises a plurality of soil moisture sensors, constructed in accordance with the present disclosure.

The exemplary embodiments provided herein are for use in irrigation agriculture, particularly permanent crops. More specifically, the exemplary embodiments comprise a system and method for accurately measuring the volumetric water content of soil using a cost effective apparatus.

For context, of the principal ways that farmers manage their irrigation is with soil moisture sensors. In brief, plants uptake their water from the soil through their root structure. Their ability to do so is impacted by the amount of water in the soil, the soil tension, and the suction force needed by the roots to absorb water.

Other sensor designs have emulated the root of a plant, and measure the water tension in the soil. These are known as tensiometers. There are sensors that look like forks that have two parallel probes about an inch apart and measure the capacitance between the probes. This is calibrated to the amount of moisture, and the calibration is dependent on the soil type that the probe measures. There are probes that use gymsum blocks that absorb water, and as these sensors absorb water their resistance reduces changes in a manner that is correlated to the amount of water absorbed. These probes have a short lifespan, as the process of absorbing moisture causes them to deteriorate. Further, their installation takes weeks before readings are meaningful.

Liquid sensing using radio frequency techniques is a known mechanism in industrial settings. One such reference would be: Liquid Sensing at Radio Frequencies, Complex impedance measurement of liquid samples as a function of frequency, Microwave Journal, Thomas J. Warnagiris, Sep. 1, 2000.

Until now, complete soil moisture sensors have not been produced in a manner that are effective for agriculture, using radio frequency sensing, that are low power, easy to install, and can measure large volumes of soil accurately.

The systems and methods provided herein include a soil moisture sensor that is highly accurate, measures a larger volume of influence than other sensors, easy to install, and operates without soil specific calibration requirements.

Soil moisture sensors disclosed herein rely on the Van der Waals bonding properties of water, which describes the force between the permanent dipole of a water molecule and the induced dipole from a radio frequency stimulus (known as the Debye force). When a radio frequency pulse stimulates water, it will move. The more water there is, the harder it is for the same power level to cause the water to move—so there is a higher effective electrical impedance.

The exemplary systems and methods provided herein measure the inductance of the soil by mutually coupling an inductor(s) in the sensor to the soil, and including that mutual inductance as part of a tank circuit in an oscillator.

Example oscillator circuits also have a reference inductance that can be switched into the oscillator circuit as an alternative inductor. The frequency is measured for the two configurations of the oscillator (one with the inductor that is mutually coupled to the soil moisture, and the second configuration of an internal inductor). The difference of the two frequencies corresponds to the moisture content of the soil being measured.

According to various exemplary embodiments, the sensor system is hosted by a head-end that may be connected either directly to a computer for making measurements, or connected to a mesh or cellular radio controller. Either of these intelligent devices power on the sensor, and the sensor responds with measurements for both a calibration (internal) frequency, and a frequency that corresponds to the inductance of the soil being measured, and the temperature of the sensor.

In various exemplary embodiments, the soil moisture sensor is controlled by a microcontroller. When powered, the microcontroller wakes up, selects an internal inductance frequency, and powers on the oscillator(s). After waiting for a settling period for the oscillator(s) to stabilize, the frequency is read by an internal counter. Settling periods are not required for every embodiment.

Then the power for the oscillator circuit is turned off, the sensor mutual inductor is selected, and the power for the oscillator is re-enabled. Also, power cycling of oscillators is not required in every embodiment.

After a settling period, the frequency is again sampled by the micro-controller. Then the oscillator is powered-off. The temperature is read with a digital thermometer. These results are then sent by the microcontroller over a serial link to the host computer (e.g., receiver). One example of such a communications link can be a shared RS-232 interface.

If there are multiple sensors installed into a larger system, each of the controllers wake up at different times, identified by a controller ID programmed in the non-volatile memory, and share the same power, ground, and serial communication signals. The communication signals are enabled by each microcontroller in a time-division manner based on device ID.

The host controller, according to various exemplary embodiments, can either apply the needed algorithms to convert the sensor counter values, and the temperature to the volumetric water content, or it may select to transmit this information this to a server for later processing in a similar manner.

The sensor requires knowing the difference in frequency between the two inductors sampled, and also the temperature of the sensor when the measurements were taken. By calibrating the values of the frequencies in both air, and fully saturated water for each sensor—one can calculate the moisture content by linearly interpolating the frequency change based on moisture content. As the oscillator is known to change its frequencies due to temperature, a further adjustment is applied, commonly known as a temperature compensation.

Using the exemplary procedures described herein, the sensor has been demonstrated to accurately measure the moisture content, independent of material the moisture is suspended in, with an R-squared correlation of 0.92 or better.

The exemplary soil moisture sensor includes a hand wound center-tap sensor inductor, that couples with soil moisture, with a characteristic inductance of 1.4 uH, 18 gauge solid copper wire wound on a half inch SharkBite PEX Tubing with Oxygen Barrier, inserted into a three quarter inch diameter PVC pipe.

FIG. 1 is an example soil moisture device 100 constructed in accordance with the present disclosure. In various embodiments, the device 100 comprises an outer tubular housing 102 and an inner tubular substrate 104. In some embodiments, sensor units of the device 100 are mounted on an outer surface of the inner tubular substrate 104. The inner tubular substrate 104 can be inserted into an outer tubular housing.

In some embodiments, the sensor unit comprises a two or more antennas, such as antenna patch 106 and antenna patch 108 mounted on an outer surface of the inner tubular substrate 104. A soil moisture sensor circuit (sensor circuit 110) is positioned between and in electrical communication with the antenna patches 106 and 108 (also see FIG. 2A). In accordance with the present disclosure, several sets of sensor units, each comprising two antennas and a sensor circuit are located along the outer surface of the inner tubular substrate 104. Each of these sensor units can be addressed using a unique identifier.

It will be understood that the antenna patches 106 and 108 function as inductors, and thus, in some descriptions the terms antenna and inductor may be used interchangeably. In some embodiments, each antenna patch can comprise one or more individual antenna elements. In one or more embodiments, each antenna patch comprises at least two antenna elements.

In various embodiments, antennas can be referred to as either an upper or lower antenna (or upper/lower inductors). In general, the designation of upper or lower relates to a position of device 100 when located in the soil. For example, antenna patch 106 is an upper inductor and antenna patch 108 is a lower inductor when the device 100 is inserted into the soil. The upper inductor will be used to sense a reference inductance and the lower inductor will be used to sense a soil moisture inductance.

The device 100 can communicate with both a receiver 111 as well as an irrigation controller 115 in some embodiments. The device 100 can control operations of the irrigation controller 115 directly or indirectly through the receiver 111. In some embodiments, the receiver 111 can comprise a server in an irrigation control system. Alternatively, the receiver can include any device that is configured to receive, transmit and/or process the messages generated by a sensor circuit 110 of the device 100. In some embodiments, the device 100 can be coupled to the irrigation controller using a cable C, the cable can be wrapped in a sheath of a metal fabric to deter rodents or prevent cutting of the cable.

Figure 2A:
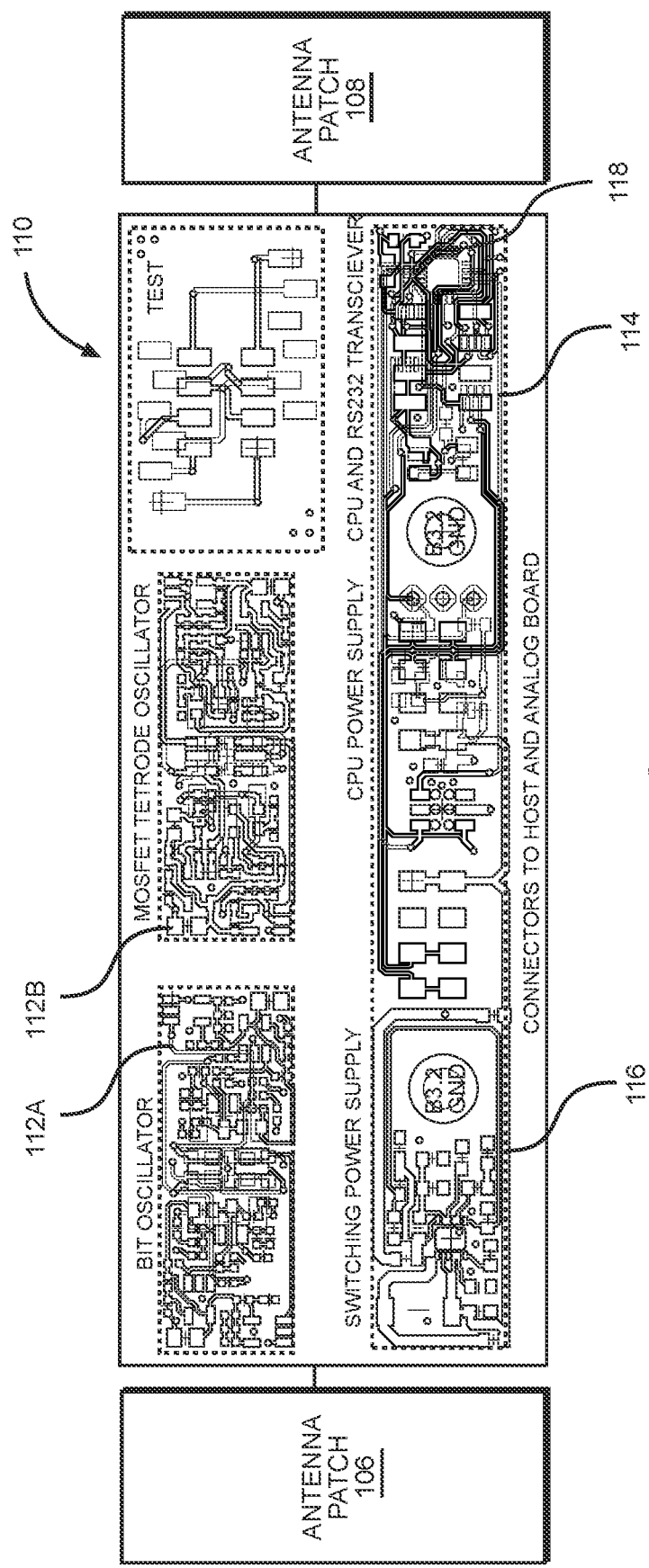
FIG. 2A is a schematic diagram of an example soil moisture sensor circuit used in a soil moisture sensor of the present disclosure.
Figure 2B:
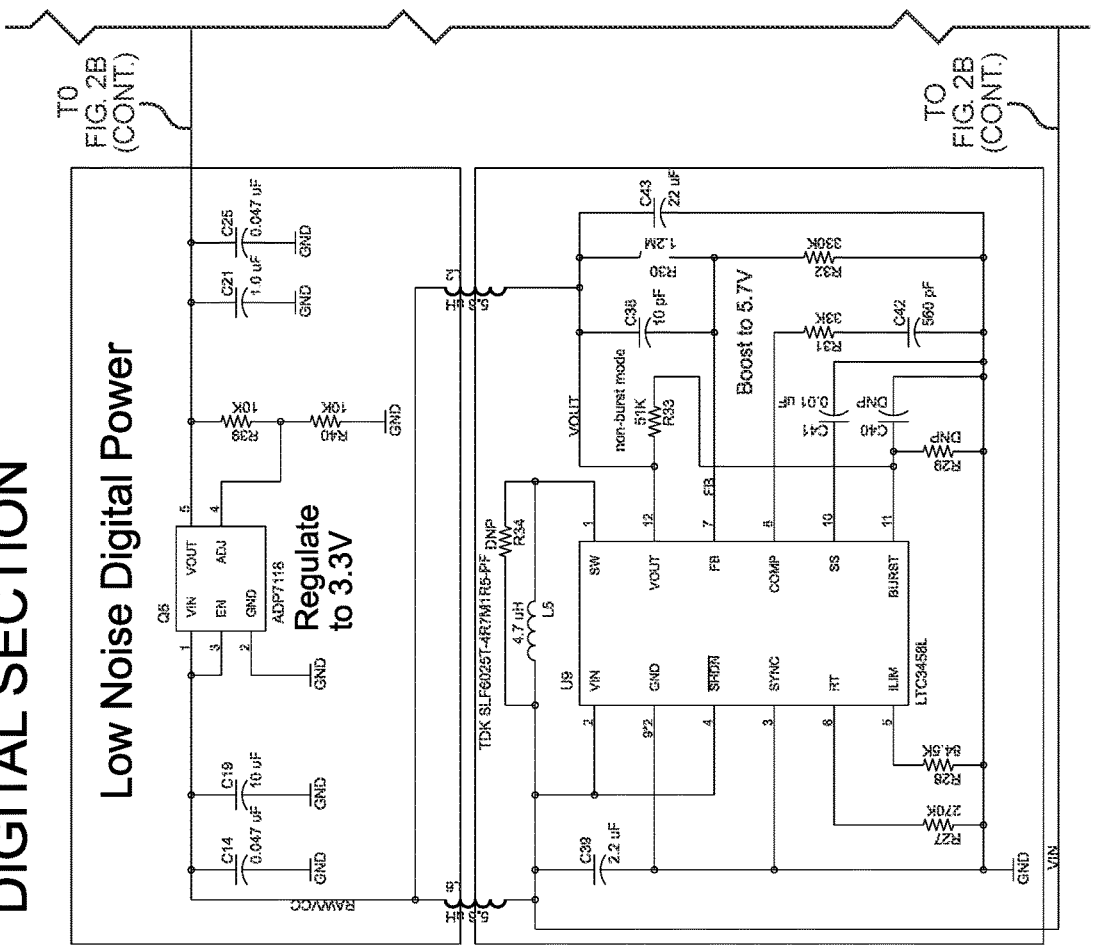
FIG. 2B is a close up of the schematic diagram of FIG. 2A.

As illustrated in FIGS. 2A and 2B, the sensor circuit 110 of FIG. 1 comprises one or more transistor circuits 112A and/or 112B, a microcontroller 114 (e.g., programmable interface circuit or PIC), a digital power supply 116, a transceiver 118, and a temperature sensor 120. In general, FIG. 2A is a macro-schematic diagram of the sensor circuit 110 and FIG. 2B is a detailed schematic diagram of the sensor circuit 110 of FIG. 2A.

Figure 2B:
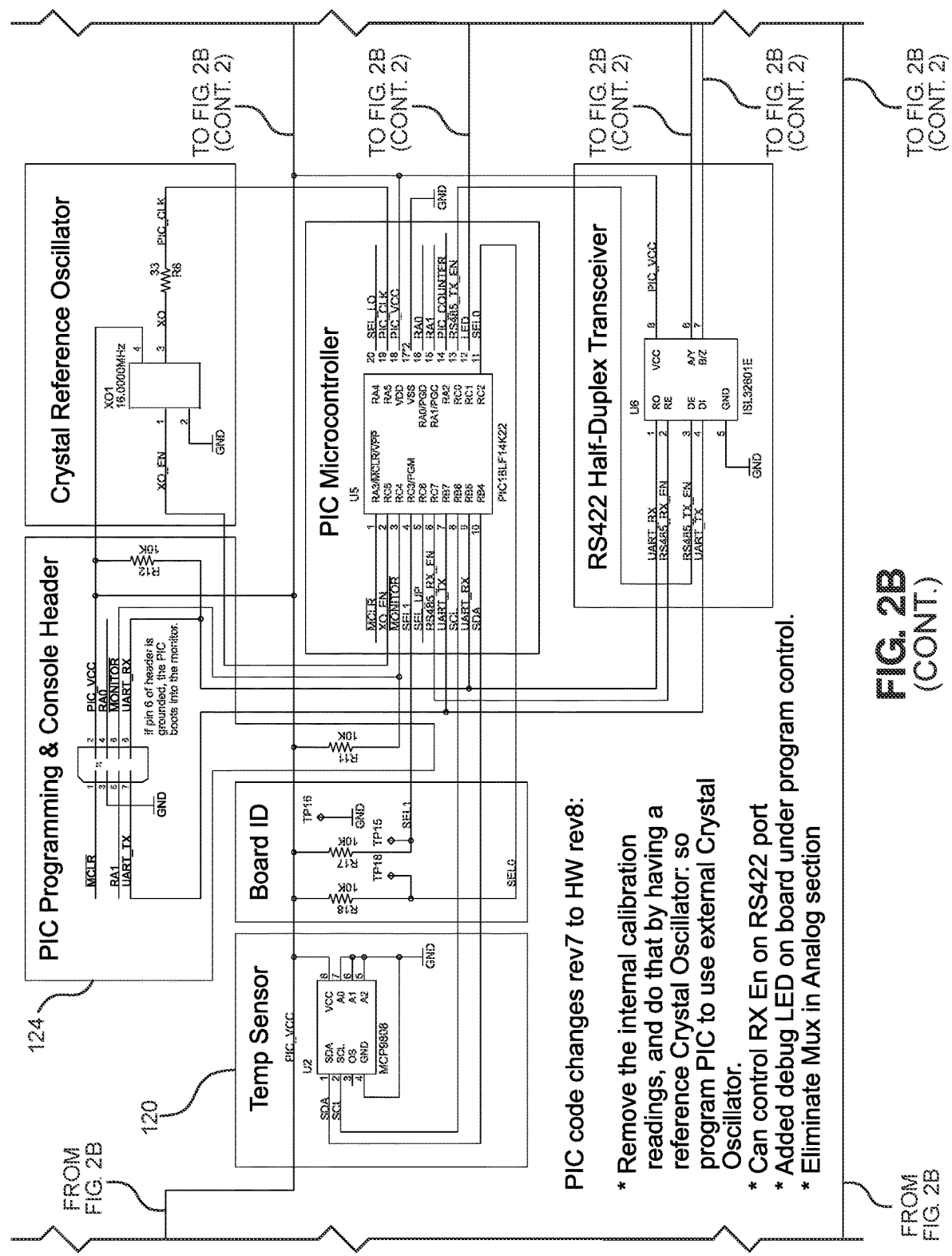

Referring to FIGS. 1-2B, the sensor circuit 110 can communicate with a receiver 111 (see FIG. 1) over a network connection 113, which can comprise a direct connection through a cellular network or indirect connection through a mesh network of other sensors. The sensor circuit 110 can also comprise a head-end that is connected either directly to a computer for making measurements, or connected to a mesh or cellular radio controller. Any of these devices such as a head-end or receiver can power on the sensor circuit 110, and the sensor circuit 110 responds with measurements for both a calibration (internal) frequency, and a frequency that corresponds to the inductance of the soil as measured, as well as a temperature of the sensor.

In various embodiments, the sensor circuit 110 can be used to selectively adjust irrigation in the area of soil that it is measuring. This can be accomplished through control of automatic pump and/or valve actuators and transducers. For example, when a soil moisture content is calculated that indicates that the area of soil has a moisture content that is below an expected moisture threshold, the sensor circuit 110 can be configured to transmit a signal that selectively adjust pumps and/or valves of an irrigation system to increase and/or decrease the flow of water to an area of soil. An example irrigation controller 115 (e.g., a sprinkler controller) can be controlled using the sensor circuit 110 or otherwise by the receiver 111.

Thus, the microcontroller can be configured to use moisture thresholds. In other embodiments, the receiver utilizes moisture thresholds and performs moisture content comparisons to these thresholds.

Thus, the microcontroller can selectively adjust operation of an irrigation system through direct or indirect control of automatic pump and/or valve actuators and transducers.

FIG. 2B also includes a detailed view of a digital section of the sensor circuit 110. In some embodiments, a digital section of the sensor circuit 110 that comprises the microcontroller 114, the digital power supply 116, the transceiver 118, and the temperature sensor 120 can also further comprise a board ID module that provides a unique device ID that is used to identify and address messages to the sensor circuit 110 on a network. The digital section can also comprise a programming and console header 124 that provides an interface that allows external devices to interact with the microcontroller 114 for programming instructions into the microcontroller 114. The programming and console header 124 also provides an interface to a digital monitor or user interface, such as a screen or touchscreen device.

In some embodiments, the transceiver 118 comprises an RS422 protocol half-duplex transceiver, although other transceivers and protocols can also likewise be utilized in accordance with the present disclosure.

In general, the transistor circuit selected for the sensor circuit 110 can comprise either a bi-junction transistor (BJT) or a tetrode transistor, such as a MOSFET tetrode. In embodiments where a BJT is used, the BJT implements two oscillators, which each couple to one of the antenna patches 106 and 108. In embodiments where a tetrode transistor is used the tetrode transistor implements two oscillators, which each couple to one of the antenna patches 106 and 108.

Figure 3:
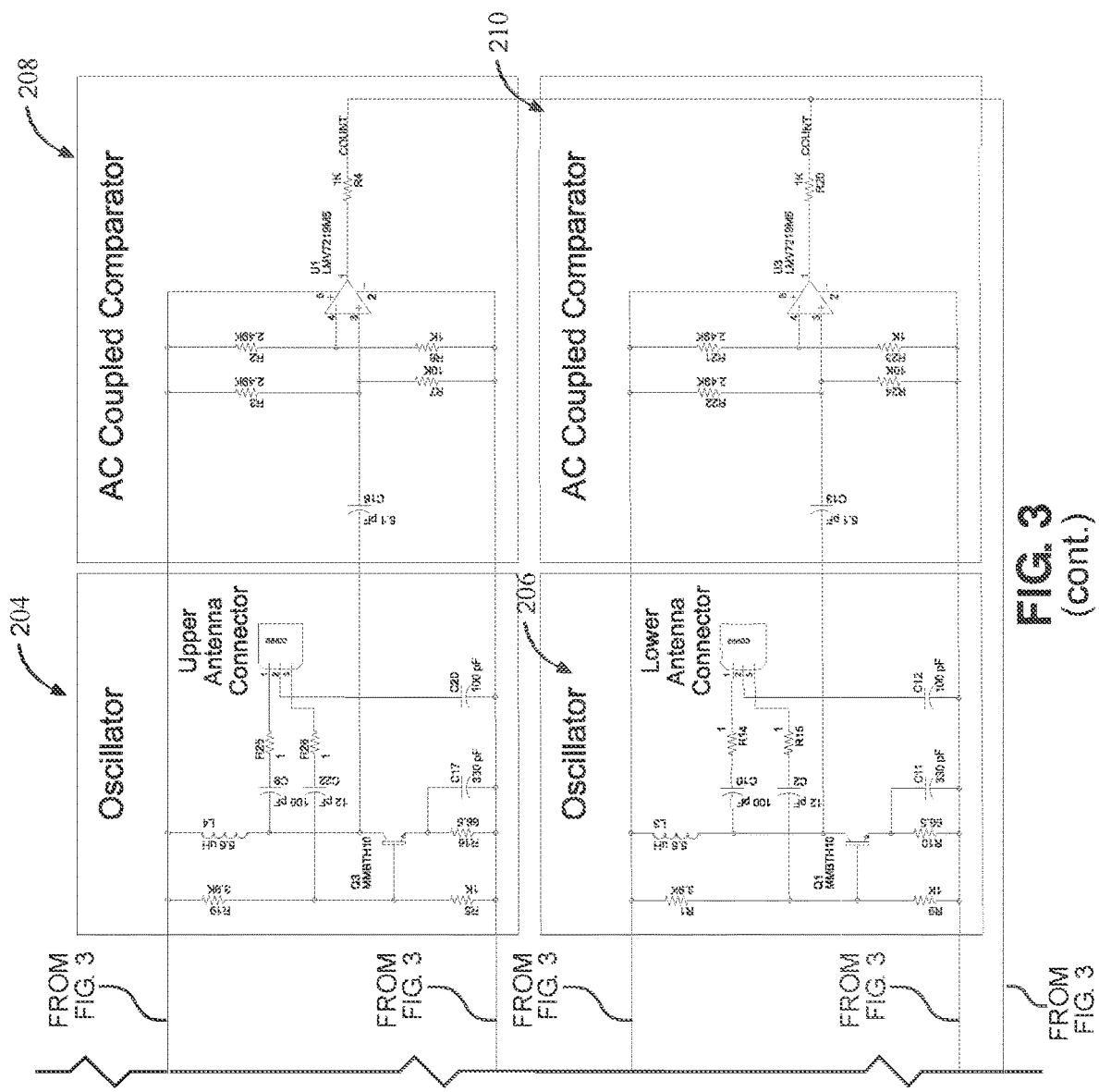
FIG. 3 is a schematic diagram of an example bi-junction transistor of a soil moisture sensor circuit of FIG. 2A.

FIGS. 1-3 collectively illustrate a transistor circuit 112A in the form of a bi-junction transistor circuit (BJT 200). The BJT 200 comprises a low noise oscillator power supply 202, a first oscillator 204 coupled with an upper antenna, such as antenna patch 106 (see FIG. 1), and a second oscillator 206, coupled with a lower antenna, such as antenna patch 108 (see FIG. 1).

A first alternating current (AC) comparator 208 counts pulses in a first inductor frequency sample, based on signals received from the first oscillator 204 using the antenna patch 106. In general, the first oscillator 204 will produce a signal with a selected frequency through the antenna patch 106. This signal is produced over a predefined time period as provided by the microcontroller 114.

A second alternating current (AC) comparator 210 counts pulses of a second inductor frequency sample, based on signals received from the second oscillator 206 using the antenna patch 108. In general, the second oscillator 206 will produce a signal with a selected frequency through the antenna patch 108. This signal is produced over a predefined time period as provided by the microcontroller 114 (see FIG. 2A).

In some embodiments, the antenna patch 106 is utilized to sense a reference inductance and antenna patch 108 is utilized to sense soil moisture inductance. It will be understood that the first inductor frequency sample is a reference inductance signal. The second inductor frequency sample is indicative of an inductance of water in the soil.

Pulses from the second oscillator 206 are counted by the second alternating current (AC) comparator 210 are referred to as soil moisture pulses, which are indicative of an inductance of the soil.

This soil moisture inductance can be compared with the reference inductance to determine a water content measurement for the soil. In some embodiments, additional processing is performed to further refine the water content measurement to account for temperature effects on the oscillators and so forth.

The outputs of both the first alternating current (AC) comparator 208 and the second alternating current (AC) comparator 210 are provided to the microcontroller 114.

Figure 4:
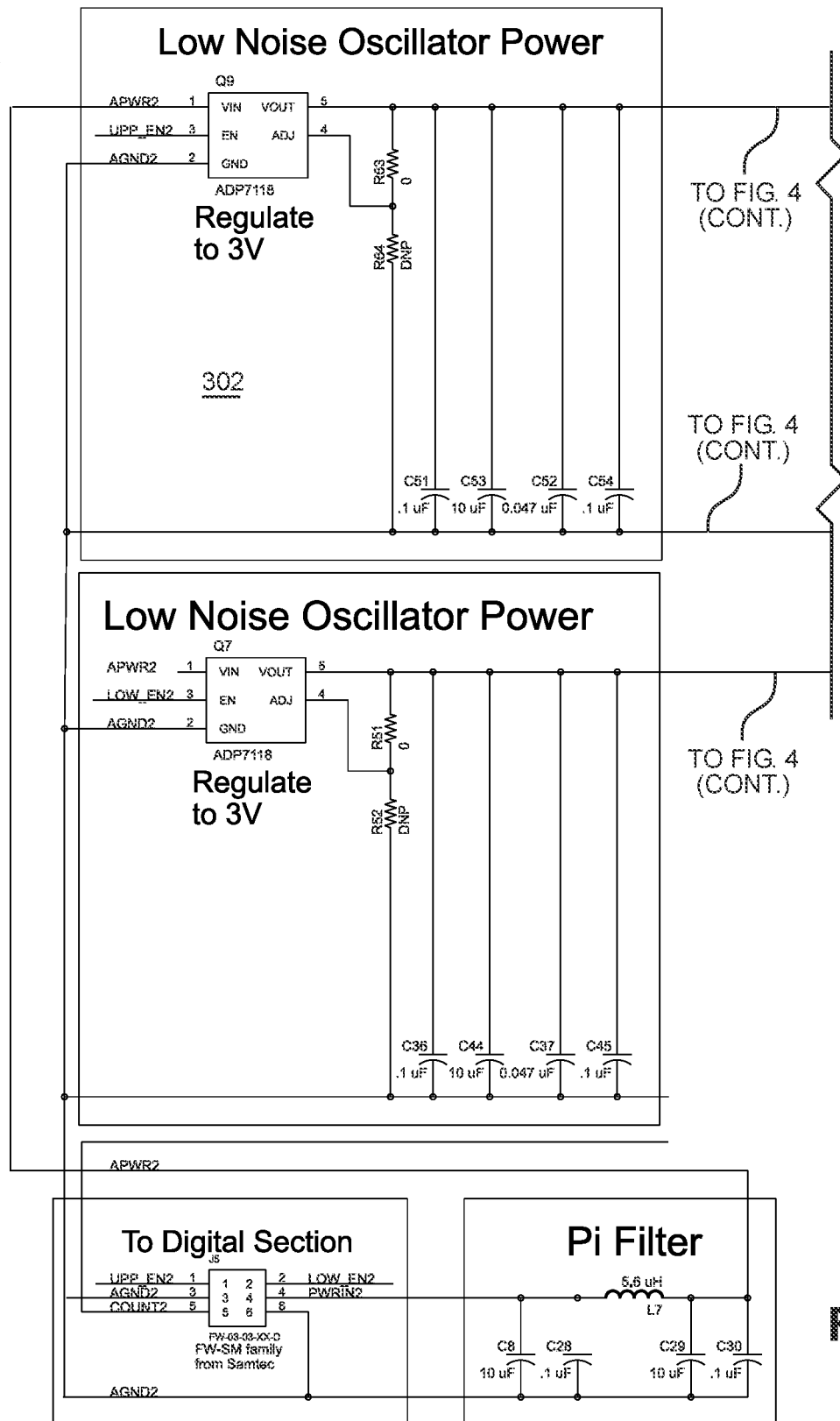
FIG. 4 is a schematic diagram of an example tetrode MOSFET of the soil moisture sensor circuit of FIG. 2A.
Figure 4:
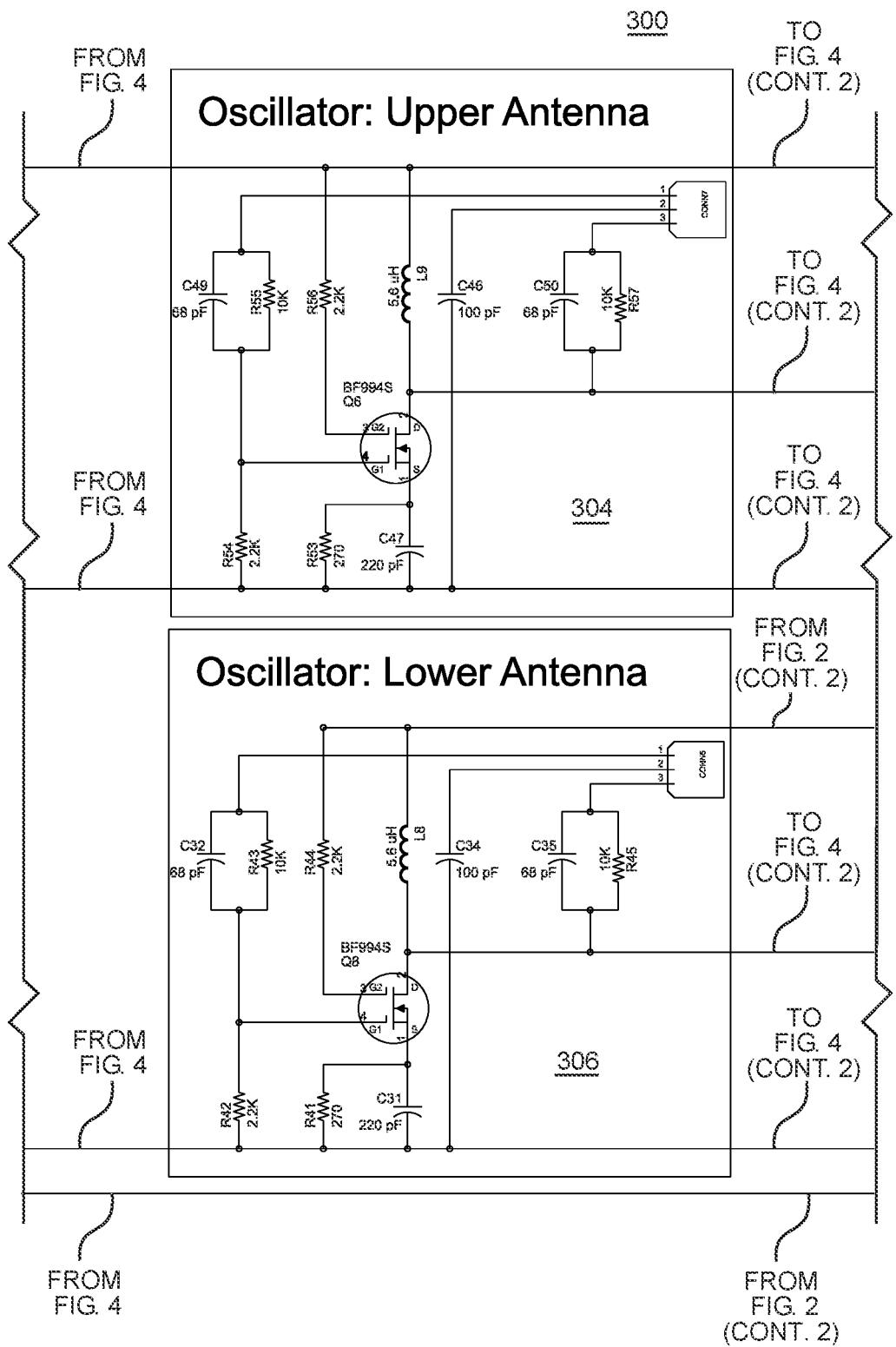
Figure 4:
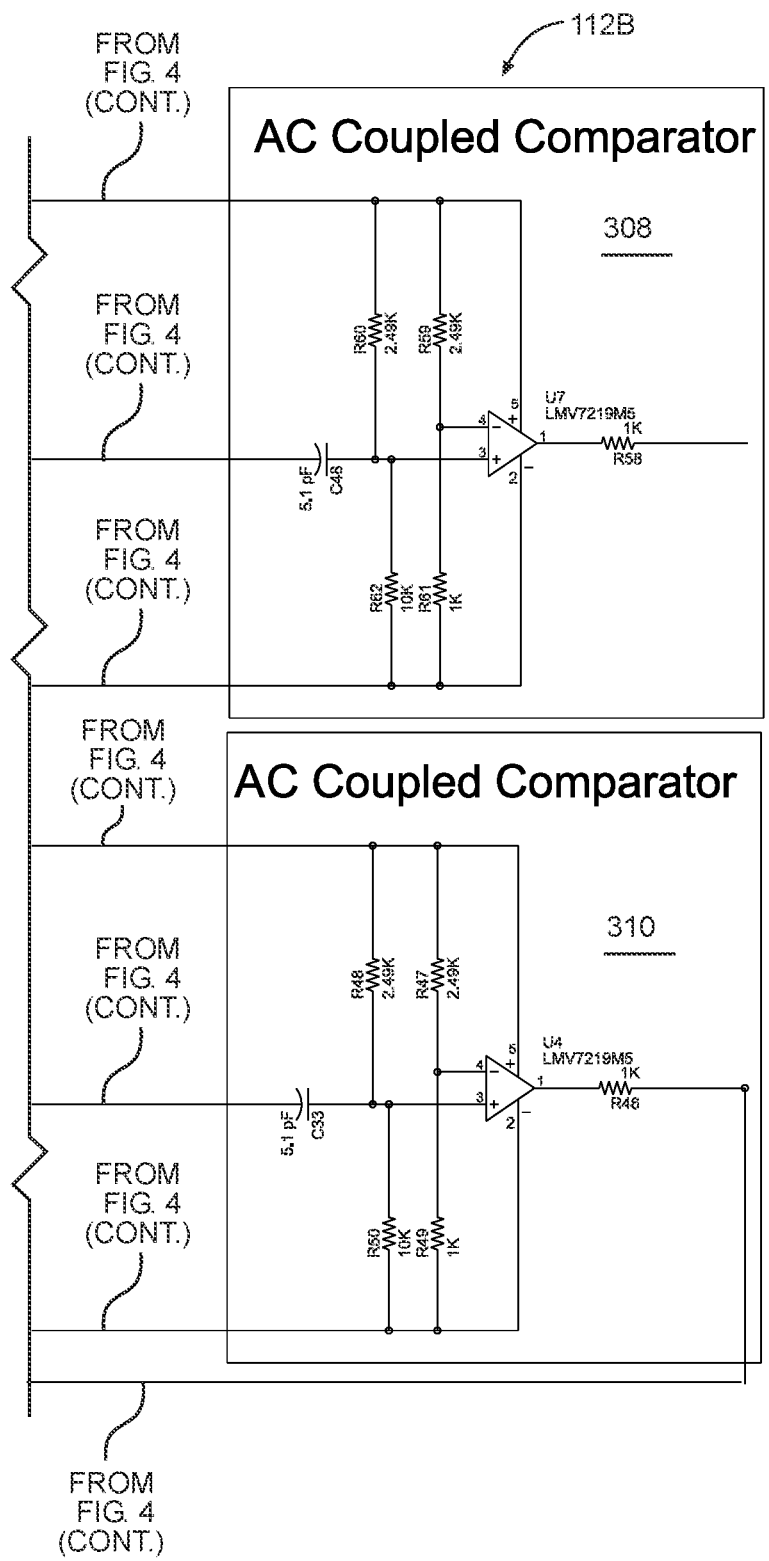

FIGS. 1, 2, and 4 collectively illustrate the transistor circuit 112B in the form of a transistor tetrode or MOSFET tetrode circuit 300. The circuit 300 comprises a low noise oscillator power supply 302, a first oscillator 304 coupled with an upper antenna, such as antenna patch 106 (see FIGS. 1 and 2A), and a second oscillator 306, coupled with a lower antenna, such as antenna patch 108. Another low noise oscillator power supply is coupled to the second oscillator 306.

A first alternating current (AC) comparator 308 counts pulses in a first inductor frequency sample, based on signals received from the first oscillator 304 using antenna patch 106. A second alternating current (AC) comparator 310 counts a second inductor frequency to create a second inductor frequency sample, based on signals received from the second oscillator 306 using antenna patch 108. The outputs of both the first alternating current (AC) comparator 308 and the second alternating current (AC) comparator 310 are provided to the microcontroller 114.

Similarly to the BJT disclosed above, the antenna patch 106 is utilized to sense a reference inductance and antenna patch 108 is utilized to sense moisture inductance in the soil.

It will be understood that the first inductor frequency sample is a reference inductance signal. The second inductor frequency sample is indicative of an inductance of water the soil. These two inductances can be compared with one another to determine a water content measurement for the soil. In some embodiments, additional processing is performed to further refine the comparative water content measurement to account for temperature effects on the oscillators and so forth.

Regardless of the transistor circuit used, the first and second comparators will output pulse counts to the microcontroller 114. The microcontroller 114 also obtains a temperature reading from the temperature sensor 120. The microcontroller 114 then transmits the pulse counts and the temperature reading on the transceiver to the receiver 111.

In some embodiments, rather than receiving pulse counts, such as reference pulse counts and soil moisture pulse counts, the microcontroller 114 can receive the first inductor frequency sample and the second inductor frequency sample. Thus, some embodiments may not require comparators. The microcontroller 114 can utilize an internal counter to count pulses in the first inductor frequency sample and pulses in the second inductor frequency sample.

In some embodiments, the sensor circuit 110 comprises both the bi-junction transistor (BJT) circuit 200 and the MOSFET tetrode circuit 300. In various embodiments, the microcontroller 114 selectively uses either the bi-junction transistor (BJT) circuit 200 or the MOSFET tetrode circuit 300. In other embodiments, either the bi-junction transistor (BJT) circuit 200 or the MOSFET tetrode circuit 300 can be removed from the sensor circuit 110 before deployment. This allows the sensor circuit 110 to be manufactured with both configurations of transistor circuits to reduce manufacturing cost.

The following use case description is from the perspective of the sensor circuit 110 using the BJT 200 of FIG. 3 in view of the schematics of the sensor circuit of FIGS. 2A and 2B. The microcontroller 114 can activate the first oscillator 204, which utilizes the antenna patch 106 to obtain a first inductor frequency sample. The oscillator 204 is powered by the low noise oscillator power supply 202. This sample is processed using the first alternating current (AC) comparator 208. The first alternating current (AC) comparator 208 counts pulses in the sample. These pulses are referred to as the reference inductance or reference pulses. In some instances, these pulses are counted over a specified period of time.

The oscillator 206 is powered by the low noise oscillator power supply 202. This sample is processed using the second alternating current (AC) comparator 210. The second alternating current (AC) comparator 210 counts pulses in the sample. These pulses are referred to as the soil moisture inductance or soil moisture pulses. In some instances, these pulses are counted over a specified period of time. This period of time can correspond in duration to the period of time when the reference inductance or reference pulses were counted.

In some embodiments, both the first oscillator 204 and the second oscillator 206 emit signals at the same frequency. In some instances, this shared frequency is above approximately 30 megahertz. The microcontroller 114 can select the frequency in some embodiments. Also, a time period for operation of the oscillators can be selected through the microcontroller 114.

The reference pulses and soil moisture pulses can be transmitted in a raw format to a receiver 111 by the microcontroller 114 over a wired or wireless link. In other instances, the comparison between the reference pulses and soil moisture pulses is determined and transmitted to the receiver 111 by the microcontroller 114.

In some embodiments, the microcontroller 114 can utilize stabilization periods for the oscillators. For example, prior to sensing inductance using the antennas, the microcontroller 114 will power the oscillators and wait for a period of time, referred to as a settling period. After the settling period has expired, inductance signals can be obtained. In some embodiments, these settling periods are not utilized.

In one or more embodiments, the microcontroller 114 can operate the oscillators 204 and 206 in a sequential manner, where reference inductance signals are obtained first and then soil moisture inductance signals are received after. In other embodiments, the oscillators are used in parallel.

In some embodiments, the microcontroller 114 is configured to post-process the reference pulses and soil moisture pulses. Again, as noted above, this post-processing can include performing comparative evaluations where a differential between the reference pulses and soil moisture pulses is determined. This differential value is representative of the moisture content in the soil.

The microcontroller 114 is programmed to either: (1) perform algorithmic processing to convert the sensor counter values (e.g., reference and soil moisture pulses) and temperature measurement to a volumetric water content value; and/or (2) transmit the sensor counter values to the receiver 111, where the receiver 111 performs these calculations.

The microcontroller 114 can thus determine a difference in pulse frequency between the two inductors sampled, along with the temperature of the sensor at a point in time when the two inductors sampled. By calibrating the values of the frequencies in both air, and fully saturated water for each sensor—one can calculate the moisture content by linearly interpolating the frequency change based on moisture content. As the oscillators change frequencies due to temperature, a further adjustment is applied, commonly known as temperature compensation.

Figure 5:
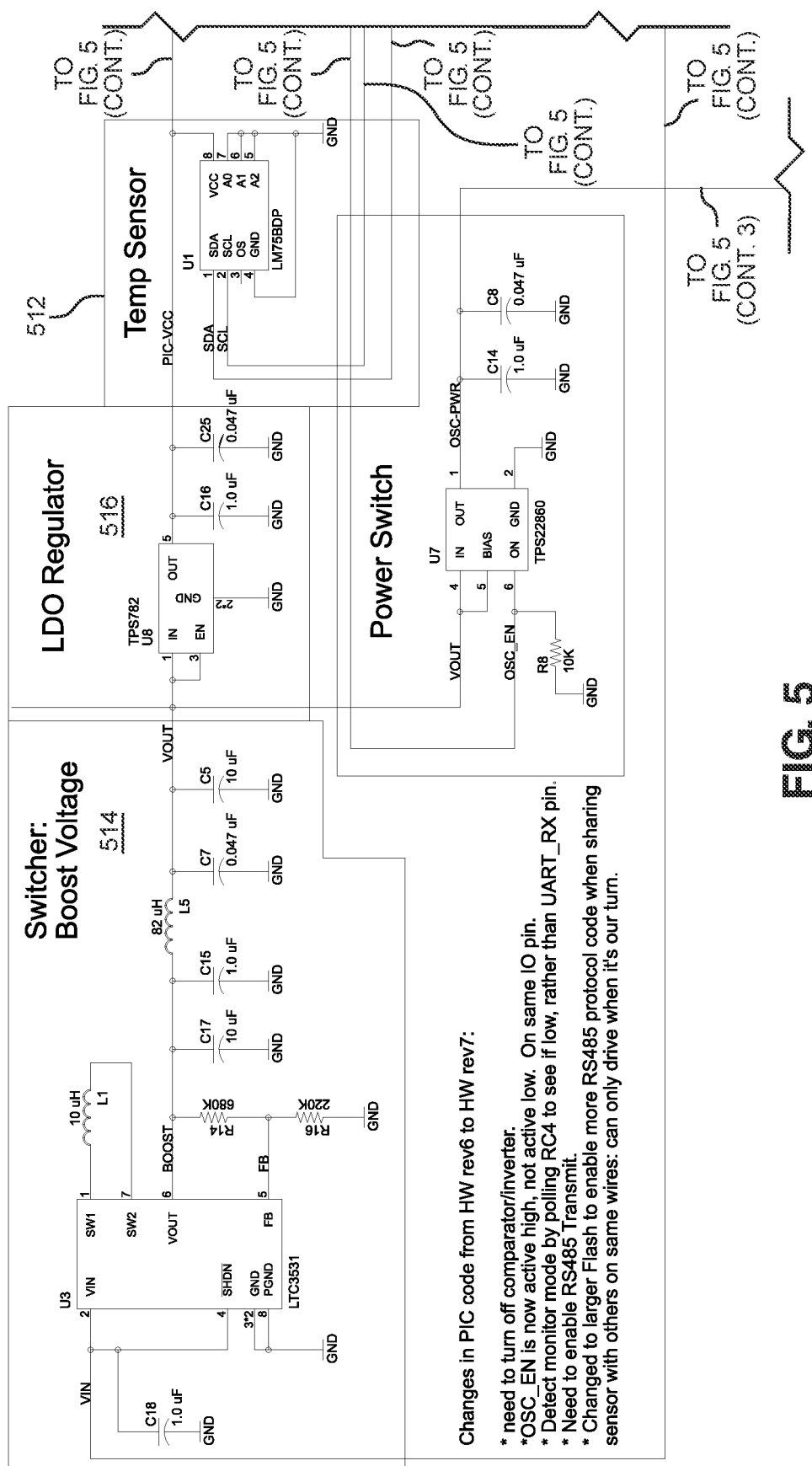
FIG. 5 is a schematic diagram of another example soil moisture sensor circuit used in a soil moisture sensor of the present disclosure.
Figure 5:
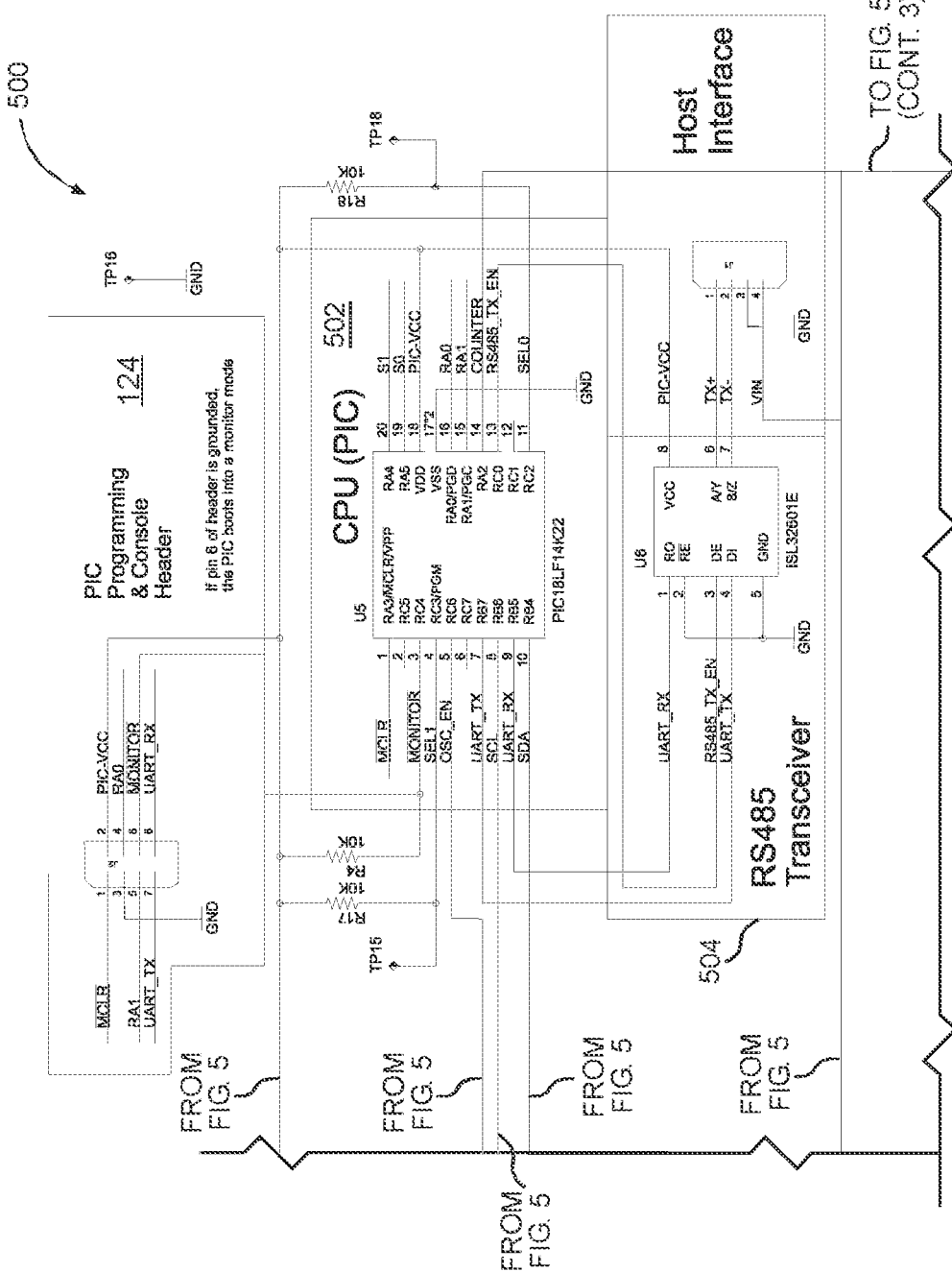

FIG. 5 is a schematic diagram of another example soil moisture sensor circuit (sensor circuit 500) that can be utilized in accordance with the present disclosure. In general, the sensor circuit 500 will utilize a single oscillator or tank circuit for two or more antennas. This configuration is in contrast with the embodiments of FIGS. 1-4 which utilized a separate oscillator for each antenna. In accordance, the sensor circuit 500 comprises a multiplexer that receives signals from the two or more antennas.

In more detail, the sensor circuit 500 comprises a microcontroller 502, a transceiver 504, an oscillator 506, a comparator 508, a multiplexing and switching module 510, and temperature sensor 512. Additional components or modules include a voltage switcher 514, a linear dropout regulator 516, a programming interface, and a power switch.

In some embodiments, the transceiver 504 receives signals or message from the microcontroller 502 such as frequency inductance samples, sample counts, soil moisture values (compensated and/or raw values), temperature readings, and so forth. As with other embodiments, these signals or messages can be transmitted to a receiver (not shown) such as a server or base station.

The oscillator 506 can comprise a bi-junction transistor in some instances. The oscillator 506 is configured to generate signals at a particular frequency. These signals are transmitted to two sets of antennas. For example, the oscillator 506 is electrically and communicatively coupled to a first set of internal inductors 520A and 520B and a second set of external or mutual inductors 522A and 522B. The oscillator 506 is coupled to the antennas through a multiplexer 524 of the multiplexing and switching module 510. To be sure, the components designated as antennas/inductors are identified on the diagram of FIG. 5 as line interfaces that connect the antenna patches to multiplexer 524.

In some embodiments, the first set of internal inductors 520A and 520B are utilized to obtain signals that are indicative of a reference inductance and the second set of external or mutual inductors 522A and 522B are used to obtain signals that are indicative of a soil moisture inductance.

The oscillator 506 can transmit a selected frequency to the first set of internal inductors 520A and 520B over a period of time to generate a first inductance sample. The oscillator 506 can transmit a selected frequency to the second set of external or mutual inductors 522A and 522B over a period of time to generate a second inductance sample. These samples are received and then multiplexed at the multiplexer 524 and then transmitted to the comparator 508.

As with the embodiments of FIGS. 1-4, the comparator 508 is used to count pulses in the samples received from the multiplexer 524. These pulse counts are indicative of reference inductance and soil moisture inductance.

After the pulse counts are obtained by the comparator 508, the pulse counts are transmitted by the comparator 508 to the microcontroller 502. As with the embodiments of FIGS. 1-4, the microcontroller 502 can perform various soil moisture calculations on the pulse counts in order to obtain a soil moisture content value. This can include compensating for the reference inductance, as well as temperature variations. Thus, in some embodiments, the microcontroller 502 can obtain temperature readings from the temperature sensor 512 over the period of time when samples were obtained.

Figure 6:
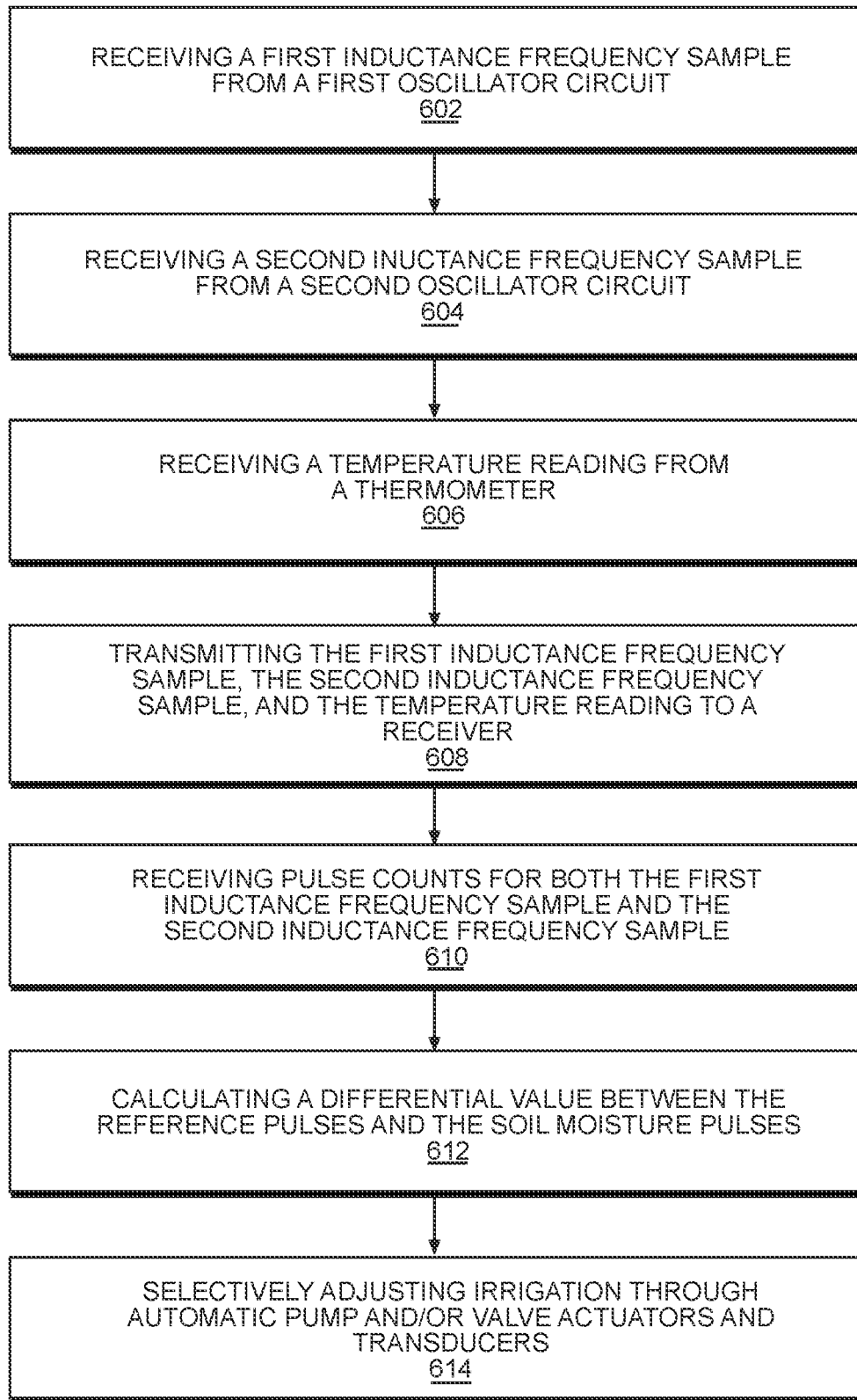
FIG. 6 is a flowchart of an example method of sensing soil moisture content in an area of soil using one or more of the soil moisture sensing devices of the present disclosure.

FIG. 6 is a flowchart of an example method of the present disclosure. The method of FIG. 6 will be understood to be executed by the microcontroller of a sensor of the present disclosure. Specifically, the method of FIG. 6 is performed within the context of the sensor circuit, such as the sensor circuit of the embodiments of FIGS. 1-4.

In some embodiments, the method includes a step 602 of receiving a first inductance frequency sample from a first oscillator circuit. As noted above, the first oscillator circuit is coupled with one or more reference inductors that sense a reference inductance. These reference inductors can include patch antennas or other similar antennas.

In various embodiments, the method includes a step 604 of receiving a second inductance frequency sample from a second oscillator circuit. Again, the second oscillator circuit is coupled with one or more mutual inductors that sense soil moisture inductance in an area of soil.

In one or more embodiments, the method includes a step 606 receiving a temperature reading from a thermometer. The temperature reading is obtained by a microcontroller during periods of time when the first inductance frequency sample and the second inductance frequency sample were obtained. These time periods can include the same time period when the first and second samples are obtained at the same time. In other instances the periods of time are distinct, such as when the first inductance frequency sample and the second inductance frequency sample are obtained at different times.

In some embodiments, the method includes a step 608 of transmitting the first inductance frequency sample, the second inductance frequency sample, and the temperature reading to a receiver. Soil moisture content can be determined by the receiver by applying one or more algorithms as disclosed herein.

In other embodiments, the microcontroller is configured to determine soil moisture content. For example, the method can include an optional step 610 of receiving pulse counts for both the first inductance frequency sample and the second inductance frequency sample. These pulse counts can be determined by a counter in the microcontroller or by way of one or more compensators that count pulses. As noted herein, the pulse count of the first inductance frequency sample is referred to as a reference pulse count. The pulse count of the second inductance frequency sample is referred to as a soil moisture pulse count.

calculating a differential value between the reference pulses and the soil moisture pulses, the differential being indicative of the soil moisture inductance Next, the method includes a step 612 of calculating a differential value between the reference pulses and the soil moisture pulses. The differential is indicative of the soil moisture inductance.

In some embodiments, the method can include processing the soil moisture inductance using techniques such as linear interpolation and temperature compensation in order to refine the soil moisture inductance.

In various embodiments, the method includes a step 614 of selectively adjusting irrigation through automatic pump and/or valve actuators and transducers. For example, when a soil moisture inductance is calculated that indicates that the area of soil has a moisture content that is below an expected moisture threshold, the microcontroller can be configured to transmit a signal that selectively adjust pumps and/or valves of an irrigation system to increase and/or decrease the flow of water to an area of soil.

Thus, the microcontroller can be configured to use moisture thresholds. In other embodiments, the receiver utilizes moisture thresholds and performs moisture content comparisons to these thresholds.

Thus, the microcontroller can selectively adjust operation of an irrigation system through direct or indirect control of automatic pump and/or valve actuators and transducers.

As noted throughout, steps 610-614 can be alternatively performed by a receiver system, such as a server in an irrigation control system.

According to some embodiments, another example soil moisture sensor can comprise a microcontroller, a single oscillator, and a single antenna. This device can be positioned inside a housing, such as the tubular housings described above. Prior deploying the sensor in an area of soil, a calibration factor for the sensor can be determined by operating the sensor in a dry environment and secondly operating the sensor in a wet environment. For example, a first inductance sample can be obtained when the sensor is in a dry environment. Pluses are counted from the first inductance sample. The device can then be submerged in water and a second inductance sample obtained. Pluses are counted from the second inductance sample. Next, a calibration factor is determined by comparison of these two pulse counts in these controlled environments. The calibration factor is a differential value between the dry sample and the wet sample in some instances. When the calibration factor is obtained, it can be stored on the microcontroller or on a server. To be sure, this calibration factor is unique to each individual sensor and can be determined by a manufacturer or an end user prior to deployment in soil.

After the soil moisture sensor is deployed into an area of soil, a frequency inductance sample is obtained using the single oscillator and antenna. When a pulse count is determined from the frequency inductance sample, the pulse count is modified by application of the calibration factor to obtain a soil moisture content value. Additional compensation for temperature changes can also be utilized to fine tune the soil moisture content value.

Some embodiments of the present disclosure can utilize a plurality of antennas as noted above. In some embodiments, these antennas can be positioned around tubular substrate. Also, sensor units (comprised of at least one antenna and one sensor circuit) can be arranged around the tubular substrate at radial offsets relative to one another. Each sensor unit can broadcast signal frequency into a discrete sector. For example, if four sensor units are deployed on the tubular substrate, each sensor unit can be clocked in its position in order to broadcast in a 90 degree radial area. Each sensor unit will broadcast in its own a 90 degree radial area with minimal overlap at the edges. In some embodiments, the sensor units can be separated by a dielectric to isolate their broadcast areas from that of other sensor units.

In one or more embodiments, the sensor circuit of a device of the present disclosure can be configured to obtain frequency samples at a plurality of frequencies. This can be advantageous in determining not only moisture content, but also constituent particulate content present in the soil moisture. For example, if water used to irrigate an area of soil becomes contaminated with salt, the sensing of the soil moisture at different frequencies can be used to determine a salinity of the water in the soil. By way of example, assume that salt moves at a frequency of 10 megahertz, but salt does not move at 30 megahertz, but water molecules will. When inductance is measured at both 10 megahertz and 30 megahertz, these values can be used to calculate an approximate salinity or salt content in the water in the soil.

Thus, the technology described herein can be utilized not only to sensing moisture content in soil, but also for measuring particulate levels in a fluid. For example, knowing inductance frequencies for salt, potassium, magnesium, lead, and other common water particulates, a sensor of the present disclosure can be tuned to different frequencies in order to obtain inductance samples at each frequency. Based on pulses counted for each of the samples, it is possible to quantify a volumetric value of each of these particulates in a water sample.

In yet other embodiments, sensor circuits of the present disclosure can be configured to vary voltage applied during inductance sampling in order to sense moisture content in soil at given distances from a sensor circuit or device. Using the devices disclosed herein, using lower to higher voltage when obtaining inductance samples, the sensor circuit(s) can obtain soil moisture content values out to specific distances from the sensor circuits. For example, at a lowest voltage, the soil moisture content values are obtained outward from the sensor circuit to a diameter of four feet. When measured at a slightly higher voltage, the soil moisture content values are obtained outward from the sensor circuit to a second diameter of seven feet. When measured at a highest voltage, the soil moisture content values are obtained outward from the sensor circuit to a third diameter of twelve feet. To be sure, these are merely example distances. The exact voltages and distances measured are a matter of sensor design and operational constraints.

According to some embodiments, a soil analysis device can be configured to include a plurality of sensor elements. In some embodiments, the soil analysis device can comprise a master element in combination with one or more slave elements in a single probe. An element as disclosed herein correlates to a sensor circuit as described above. Generally, the soil analysis device can include two types of sensor circuits/elements, (1) a master element; and (2) one or more slave elements.

The master and/or slave elements are fully configured to obtain soil moisture and/or temperature measurements disclosed above. The master and/or slave elements can include any and all of the circuits and/or components of the embodiments of FIGS. 1-6 disclosed above, in addition to the components and/or features disclosed below.

Figure 7:
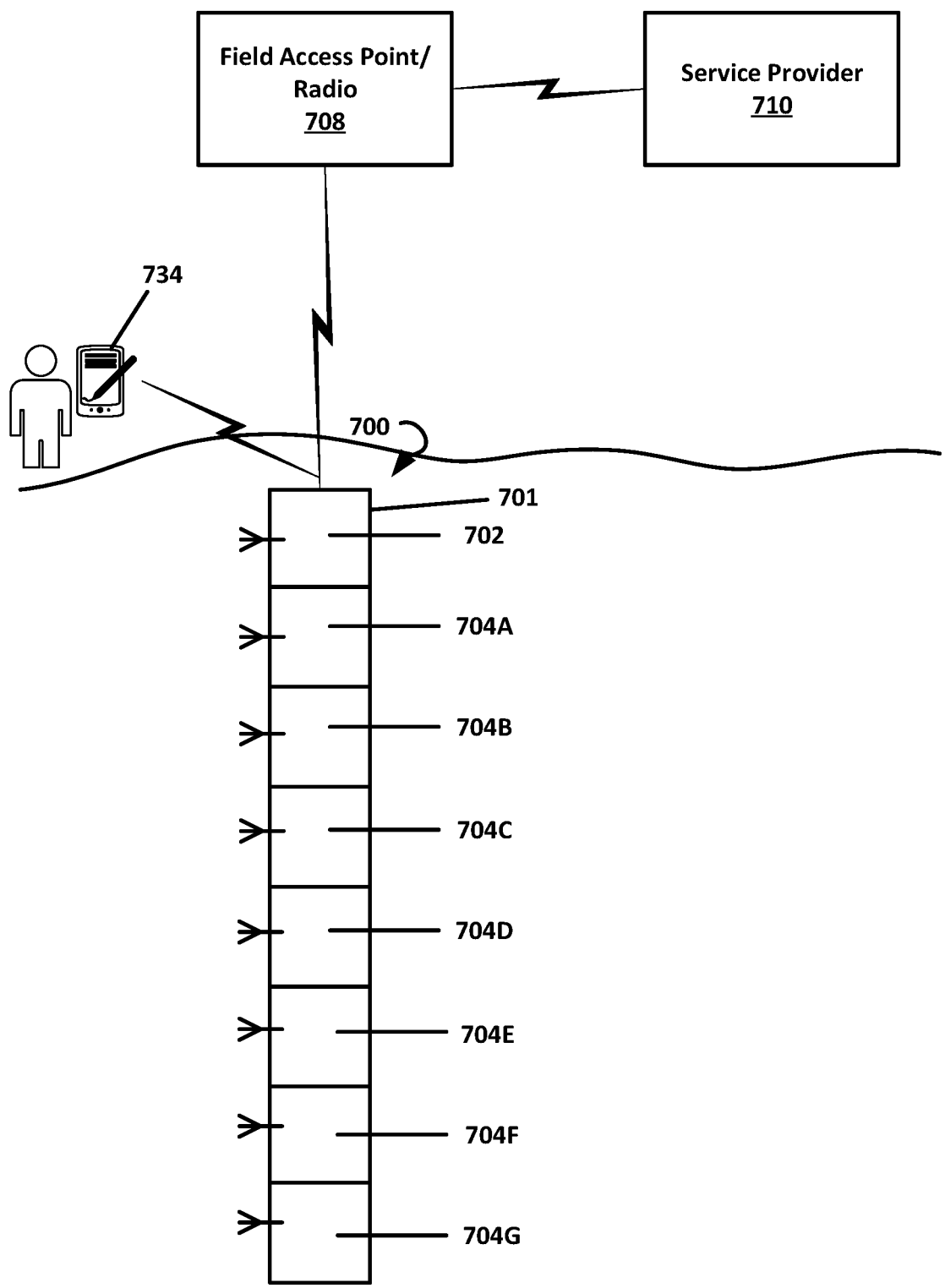
FIG. 7 is a perspective view of an example soil analysis device of the present disclosure having both master and slave elements (sensor circuits).
Figure 7:
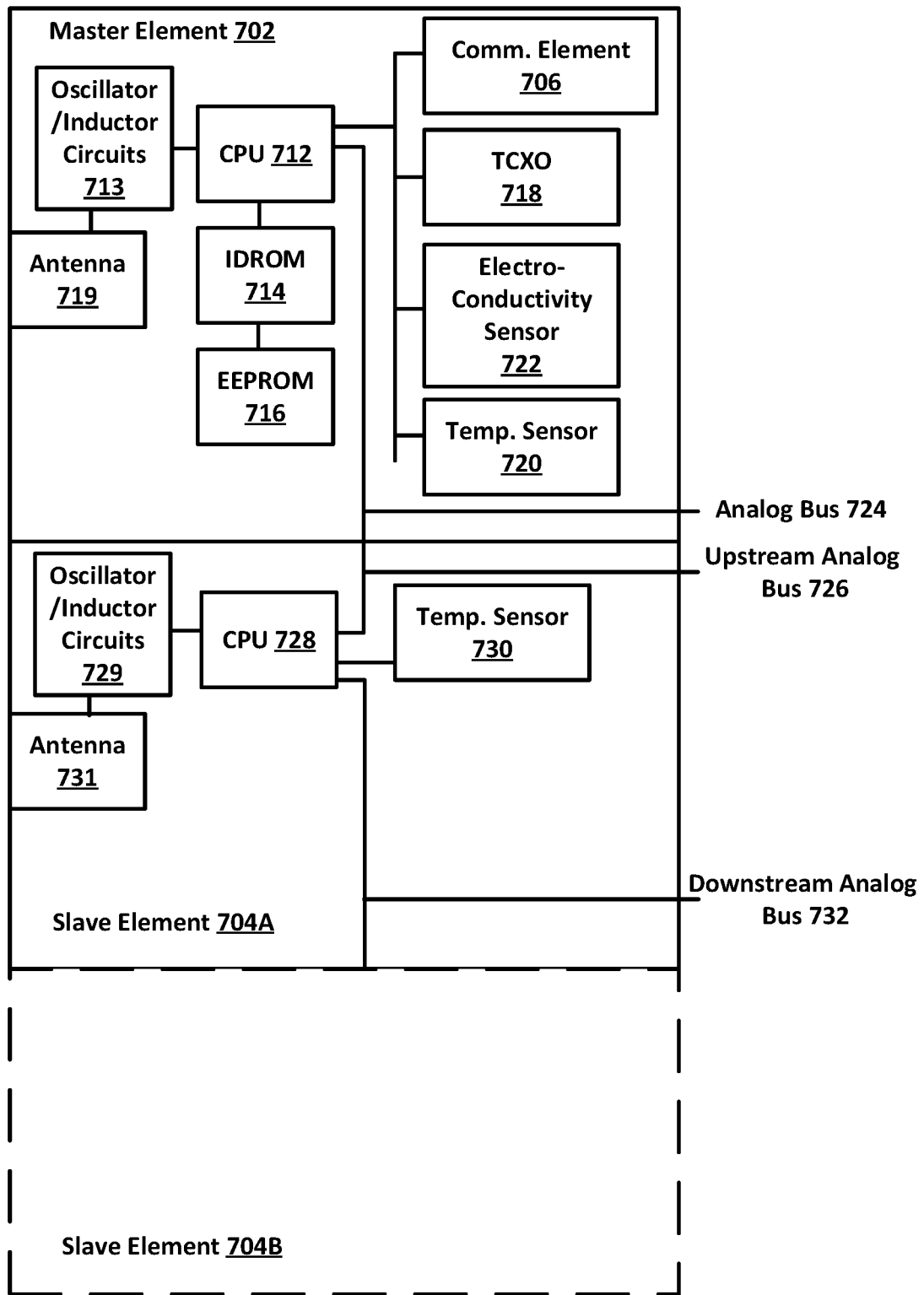

The master element can be arranged in vertical alignment with each of the one or more slave elements. The master element and slave elements are communicatively and electrically coupled in a vertically oriented daisy-chain arrangement in one embodiment. As illustrated in FIG. 7, an example soil analysis device (device 700) comprises a master element 702 and a plurality of slave elements 704A-704G. Example schematic diagrams for the master element 702 are disclosed herein with respect to FIG. 10. Example schematic diagrams for a slave element, such as slave element 704A, are disclosed herein with respect to FIG. 11.

To be sure, the device 700 can have fewer or additional elements compared to the device 700. These various elements can be housed in an enclosure 701. The enclosure 701 can be manufactured from a plastic or polymer such as polyethylene (PE), polypropylene (PP), or polycarbonate (PC), or the like that possesses better signal transmission properties than poly-vinyl carbonate (PVC). Each of these plastics allow for propagation of at least twice the signal at the same power level for the frequencies used in the soil analysis devices disclosed herein.

It will be understood that the master element 702 and slave elements 704A-704G can each include any of the sensor components of the soil moisture device 100 described above for obtaining soil moisture readings.

To be sure, PVC has an attenuation of approximately 30% for frequencies at 100 MHz. All poly-materials have better electrical characteristics at 100 MHz: it has about 1% near field attenuation, and hence—the signal sent out to the soil and returned from the soil is approximately twice as strong: hence, the sampling region is increased for the same power, and the sampling power is reduced—as less time is needed to sample for the same accuracy by a factor of two, reducing the power in half relative to using PVC as an enclosure.

In general, the master element 702 can comprise a communications element 706 that allows the device 700 to participate in long or short-range communications with an in-field access point or radio 708 using a communications element 706. This could include a local area wireless network, a cellular network, or other similar communications protocols. In some embodiments, the communications element 706 can utilize Blue-tooth Low Energy Radio, or a simple FSK (frequency-shift keying) radio in an ISM (Industrial, Science, Medical) band. In some embodiments, the in-field access point or radio 708 could be a repeater that relays data from a plurality of devices in a particular geographical area to a service provider 710 (e.g. backend data processing and storage service).

The master element 702 can utilize a primary battery cell, such as a Lithium Thionyl Chloride 3.6 VDC battery that has very dense power capacity and long shelf and use life. To be sure, other power sources can be utilized as would be known to one of ordinary skill in the art.

The master element 702 can also comprise a CPU 712 (central processing unit) that is configured to control the various components of the device 700. Generally, the CPU 712 includes a processor and memory that store firmware/hardware that can be executed by the processor to perform methods disclosed herein and control functions of device components. The CPU 712 may include an individual selection number ROM 714 (hereinafter referred to as an IDROM 714) and a serial EEPROM 716. The master element can assign and store unique values for each of the slave elements using the IDROM 714.

Moreover, the master element 702 and slave elements 704A-704G can each include any of the elements of the soil moisture device 100 described above required to obtain soil moisture readings. For example, the master element can include oscillator/inductor circuits 713 that can be controlled by the CPU 712. The oscillator/inductor circuits 713 can include any of the circuits disclosed above (such as the elements illustrated in FIGS. 2-5) that are used to generate signals that are transmitted by the antenna 719. That is, the oscillator/inductor circuits 713 can emit either or both of a first inductance frequency and a second inductance frequency, as well as receive responsive signals from the soil that can be interpreted by the CPU 712 or a service provider.

The master element 702 can also comprise a temperature compensated crystal oscillator (TCXO 718), a temperature sensor 720, an electro-conductivity sensor 722, and an analog bus 724, each of which will be discussed in greater detail herein. The TCXO 718 can function as a digital clocking element for the master element 702. The master element 702 can comprise an antenna 719 that emits signals into and receives signal from an area of soil as disclosed in the embodiments described supra.

The temperature sensor 720 can be controlled to obtain soil temperature measurements at discrete points in time.

The temperature sensor 720 can comprise a thermistor or other similar device. The electro-conductivity sensor 722 can be utilized to determine or infer fertilizer content by measuring electro-conductivity in a low-power manner. For example, the CPU 712 can implement a short sampling time (or other power reducing strategy) for the electro-conductivity sensor 722 to enable measuring electro-conductivity in a low power manner without requiring opposing polarities on electrodes of the electro-conductivity sensor 722 to prevent ionization and loss of accuracy over time. Generally, the master element 702 is communicatively coupled with the slave element 704A. Each of the plurality of slave elements 704A-704G are constructed identically to one another. For purposes of brevity and clarity, the construction of slave element 704A is discussed. The slave element 704A comprises an upstream analog bus 726, a CPU 728, oscillator/inductor circuits 729, a temperature sensor 730, an antenna 731, and a downstream analog bus 732.

The oscillator/inductor circuits 729 can include any of the circuits disclosed above (such as the elements illustrated in FIGS. 2-5) that are used to generate signals that are transmitted by the antenna 731. That is, the oscillator/inductor circuits 729 can emit either or both of a first inductance frequency and a second inductance frequency, as well as receive responsive signals from the soil that can be interpreted by the CPU 728 or a service provider.

In general, the upstream analog bus 726 is communicatively coupled to the analog bus 724 of the master element 702. The antenna 731 can be used for emitting signals into and receiving signals from the soil. The downstream analog bus 732 would be coupled to an upstream analog bus of another slave element connected below the slave element 704A, such as slave element 704B. The plurality of slave elements 704A-704G are connected in series from top to bottom, with slave element 704A being directly coupled to the master element 702. In some embodiments, the analog bus disclosed herein are 1-bit analog, but other suitable substitutions can be made as desired. Thus, the device 700 is configured for 1-wire data communications to reduce circuit cost resulting from a reduction in connector pins and lower power consumption overall.

The master element 702 can be configured to automatically determine how many channels (e.g., slave elements) are present in the device 700, the depth of each channel. The slave elements can be daisy-chained from a bottom (e.g., lowest slave element) of the device 700 to a top (e.g., master element 702) of the device 700 in a modular fashion. Thus, channels/slave elements can be added or subtracted in a plug-and-play manner. Each slave element include the same firmware that can include either with hardware (dipswitches), or with firmware (EEPROM).

As noted above, the device 700 can couple with the service provider 710. The service provider 710 can process the data obtained from one or more devices. For example, the service provider 710 can implement machine learning to determine moisture levels to tune specific responses in the field to the detected (inferred) soil type without requiring soil tests. For example, as irrigation occurs in the field, a wilting point and a field saturation point can be inferred from moisture levels. These determinations can be coupled with a percolation rate to infer a soil type and tune the calibration of the device 700 for the specific site, installation, and specific soil type.

In one embodiment, the master element 702 can operate from the surface of the soil to a depth of approximately three inches. Slave element 704A has its antenna positioned to operate at a depth of nine inches. Slave element 704B has its antenna positioned to operate at a depth of fifteen inches. Slave element 704C has its antenna positioned to operate at a depth of 21 inches. Slave element 704D has its antenna positioned to operate at a depth of twenty seven inches. Slave element 704E has its antenna positioned to operate at a depth of thirty three inches. Slave element 704F has its antenna positioned to operate at a depth of thirty nine inches. Slave element 704G has its antenna positioned to operate at a depth of forty five inches. To be sure the antenna of each element may be located approximately at the midline or centerpoint of the element. Based on the auto-discovery methods disclosed herein, the master element can be configured to obtain readings at specific depths in the soil based on the known depth of each slave element and the recorded order of the slave elements and their unique identifiers. That is, the vertical location of the slave elements in the stack is indicative of their depth.

The device 700, and specifically master element 702 can be configured to automatically configure each of the slave elements and allow for data transfer through the stack of elements (both master and slave(s)). As noted above the elements are connected over a bus (which could include a trace or wire). Each wire connecting two elements (either master/slave or slave/slave) can be used for bidirectional communication. For example, the master element 702 can drive its output signals as an active low signal rather than using high signals to reduce electrical contention.

Initially, the CPU 712 of the master element 702 can wake up. The wake up can be programmed into the CPU 712 or triggered from a wake up signal over the network or even from a handheld unit 734. For example, a user could utilize the handheld unit 734 to wake the CPU 712 with a signal. The user can read information from the device 700 using the handheld unit 734. In some embodiments, the handheld unit 734 can communicate over a short-range, active or passive method such as NFC (near-field communications), Bluetooth, RF (radio frequency), and the like.

The master element 702 can output a 10 millisecond low pulse signal in order to begin the process of channel synchronization. The slave element 704A receives the signal and responds with a 20 millisecond pulse by driving its output low. If the CPU 712 of the master element 702 determines that the analog bus 724 has a low signal after the master element 702 stops outputting its signal, then the CPU 712 knows that it has detected a slave downstream. The master element 702 can transmit a unique identifier (such as 1) to the slave element 704A. The slave element 704A can repeat this process to determine if another slave element is connected, such as slave element 704B. If another slave element is found, the master element 702 pushes down a unique identifier to the newly discovered element. This process can repeat until the last slave element attempts to locate another downstream slave element and no response is received. When the last slave element is identified (by lack of a downstream response), then that slave element reports back upstream the last slave has been found, and each intermediate slave element repeats the message up to the master element.

Each slave element (as well as the master element) can perform the signal emission and receipt process to obtain inductance frequency samples that are used to determine soil moisture content. The slave elements can also obtain temperature readings.

As data are obtained by each of the slave elements, the slave elements can use a data process to send their data upstream to the master element. The protocol to pass data between two sub-systems can use a downward edge to start a timer, and then samples the line (analog bus) later to determine the value being transmitted. This process provides a bit level means of transmitting data; and from that a synchronization means to frame bytes. In some embodiments, the master element can pass a command through the stack of slaves (or even addressed to a specific slave by its ID) to read moisture content and temperature. When the master receives these data from one or more of the slave elements, the master element can transmit the received data over the network or to the handheld unit 734.

Figure 8:
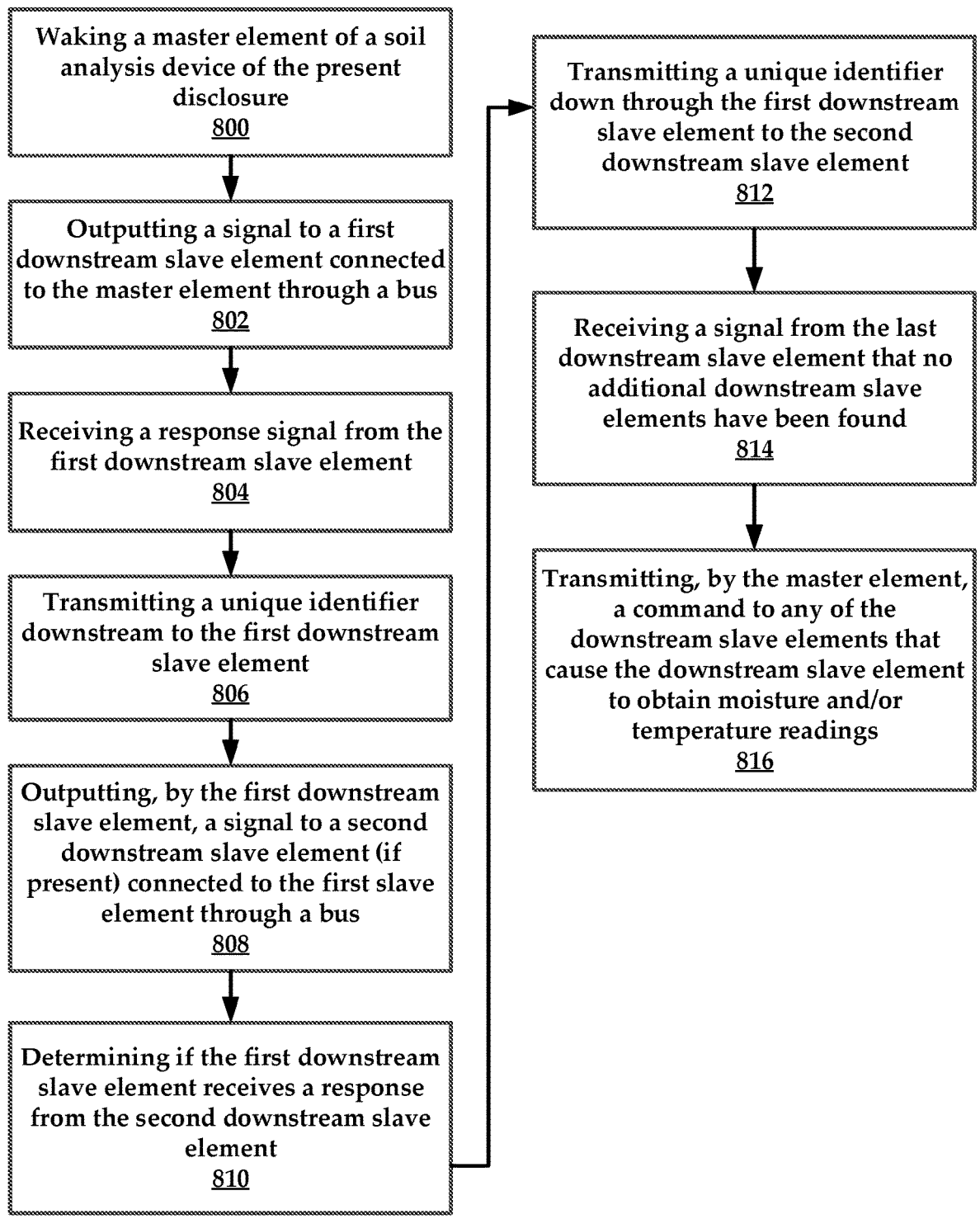
FIG. 8 is a flowchart of an example auto-discovery method of the present disclosure.

FIG. 8 is a flowchart of an example method of the present disclosure. The method can include a step 800 of waking a master element of a soil analysis device of the present disclosure. The method can include a step 802 of outputting a signal or pulse to a first downstream slave element connected to the master element through a bus. Next, the method includes a step 804 of receiving a response signal or pulse from the first downstream slave element. In some embodiments, the response signal differs from the signal output by the master element. As noted above, the response pulse can have a period (20 ms) that is double that of the period (10 ms) of the pulse received from the master element.

When the response signal is received, the method includes a step 806 of transmitting a unique identifier downstream to the first downstream slave element. The first downstream slave element can be addressed using this unique identifier. The unique identifier can be generated and/or stored using an IDROM disclosed above.

The method can include a step 808 of outputting, by the first downstream slave element, a signal to a second downstream slave element (if present) connected to the first slave element through a bus. The method includes a step 810 of determining if the first downstream slave element receives a response from the second downstream slave element. If a response is received, the method can include a step 812 of the master element transmitting a unique identifier down through the first downstream slave element to the second downstream slave element. This process can be repeated for as many slave elements are present in the stack. When the last downstream slave element does not receive a response to a signal transmitted downstream, the method can include a step 814 of receiving a signal from the last downstream slave element that no additional downstream slave elements have been found.

In some embodiments, the method can include a step 816 of transmitting, by the master element, a command to any of the downstream slave elements that cause the downstream slave element to obtain moisture and/or temperature readings. The command can include the unique identifier(s) for the downstream slave element(s) that are to obtain readings. The slave elements can report their data up through the stack to the master element.

In one embodiment, the master element can transmit the data obtained from the one or more slave elements to a receiver, such as a service provider or handheld unit. In some instances, the data are transmitted by the master element to a repeater or field unit for relay to a network such as a cellular communications network.

Figure 9:
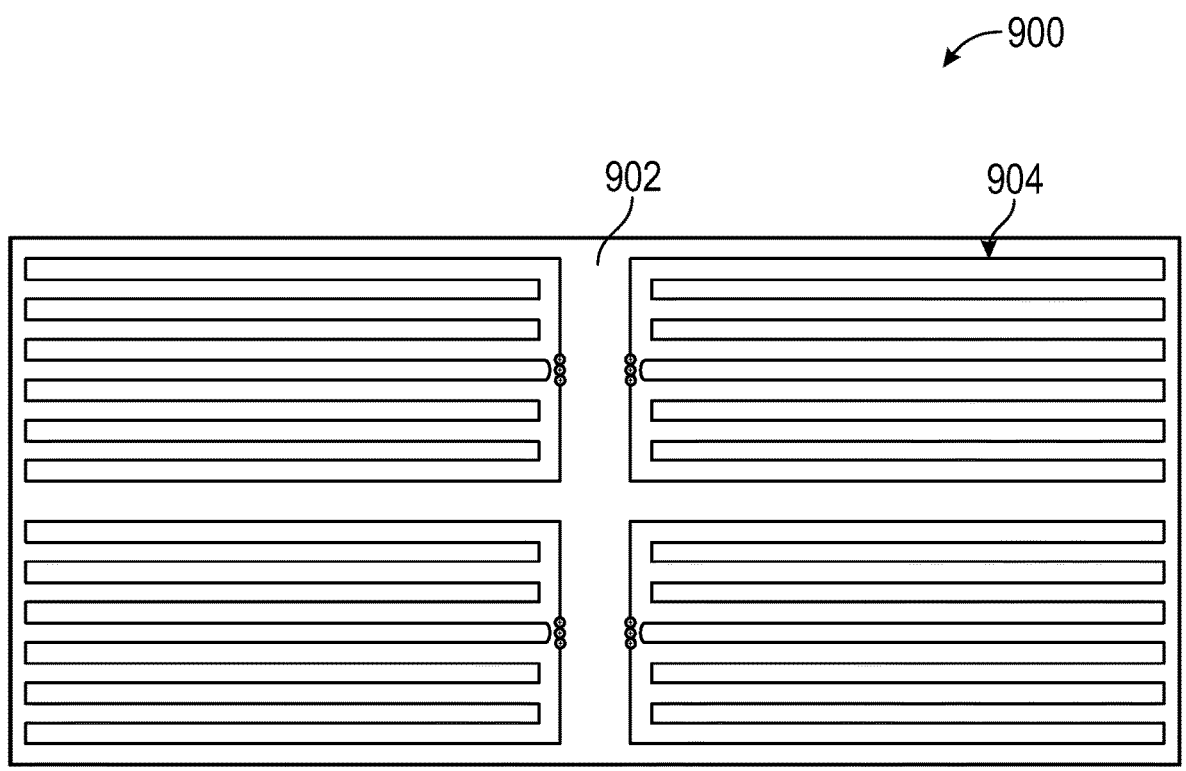
FIG. 9 is a plan view of an example antenna for use in various embodiments.

FIG. 9 illustrates an example antenna 900 that can be utilized in any of the master or slave elements disclosed above. In some embodiments, the antenna 900 is a single sided configuration on a dielectric substrate 902 such as capstan (e.g., flex circuit). To be sure, a single sided antenna has better performance and its performance does not change as temperature changes. That is, as the dielectric substrate 902 (capstan) changes size with temperature but the separation of the trace patterns 904 on the antenna does not change (as they are all printed on one side). This configuration provides 10X improved performance over temperature. Prior to this change, temperature change may cause the oscillator to change with nearly the same magnitude (in an opposite direction) that an irrigation event would cause (i.e., temperature getting colder at night would increase the frequency; moisture increasing would decrease the frequency)—the magnitude of the increase (for temperature) was about the same as the magnitude of the decrease (for moisture). In this example, there are four trace patterns on the dielectric substrate 902 but fewer or more can be present.

Figure 10:
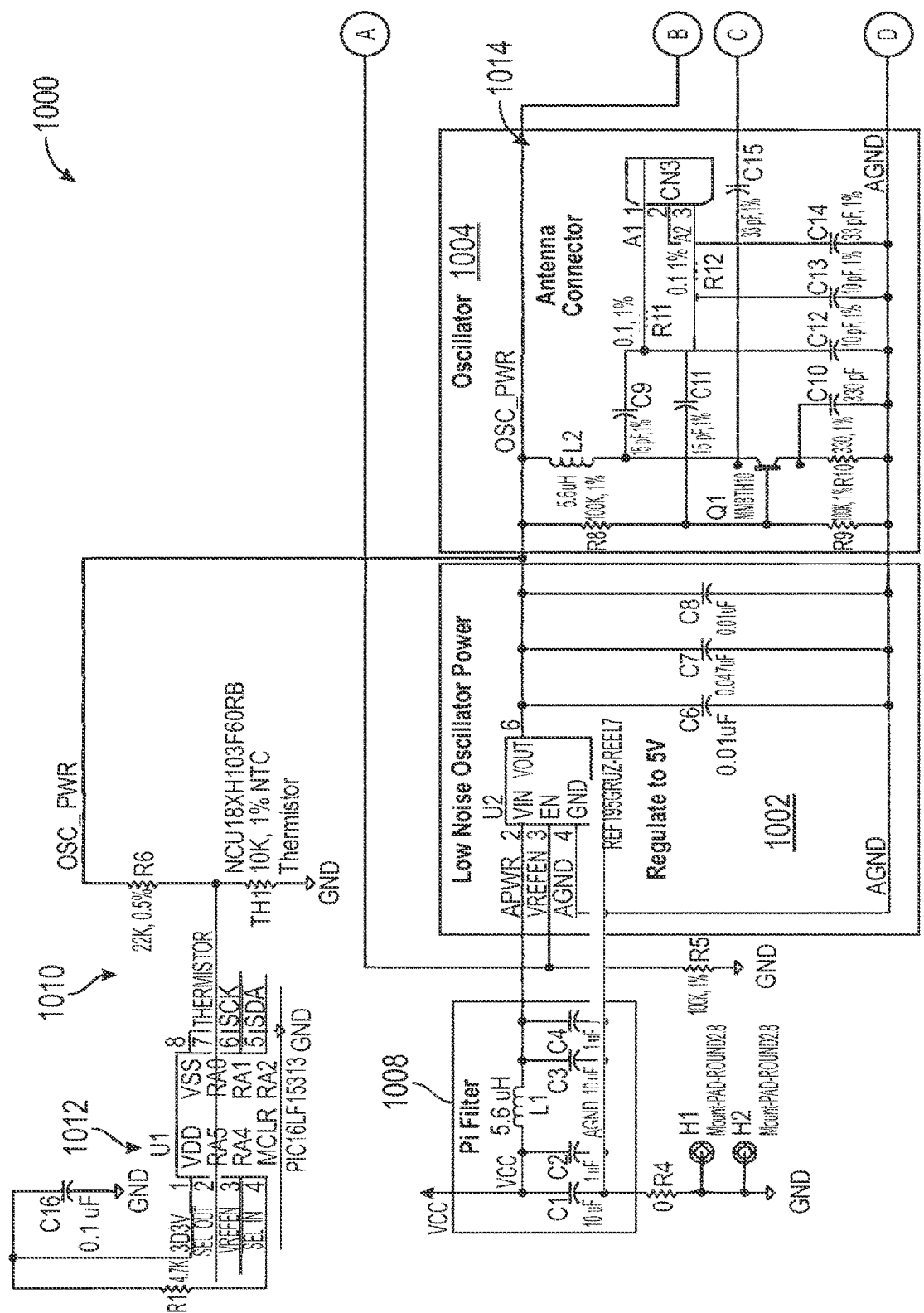
FIG. 10 is a schematic circuit diagram for a master element of the present disclosure.
Figure 10:
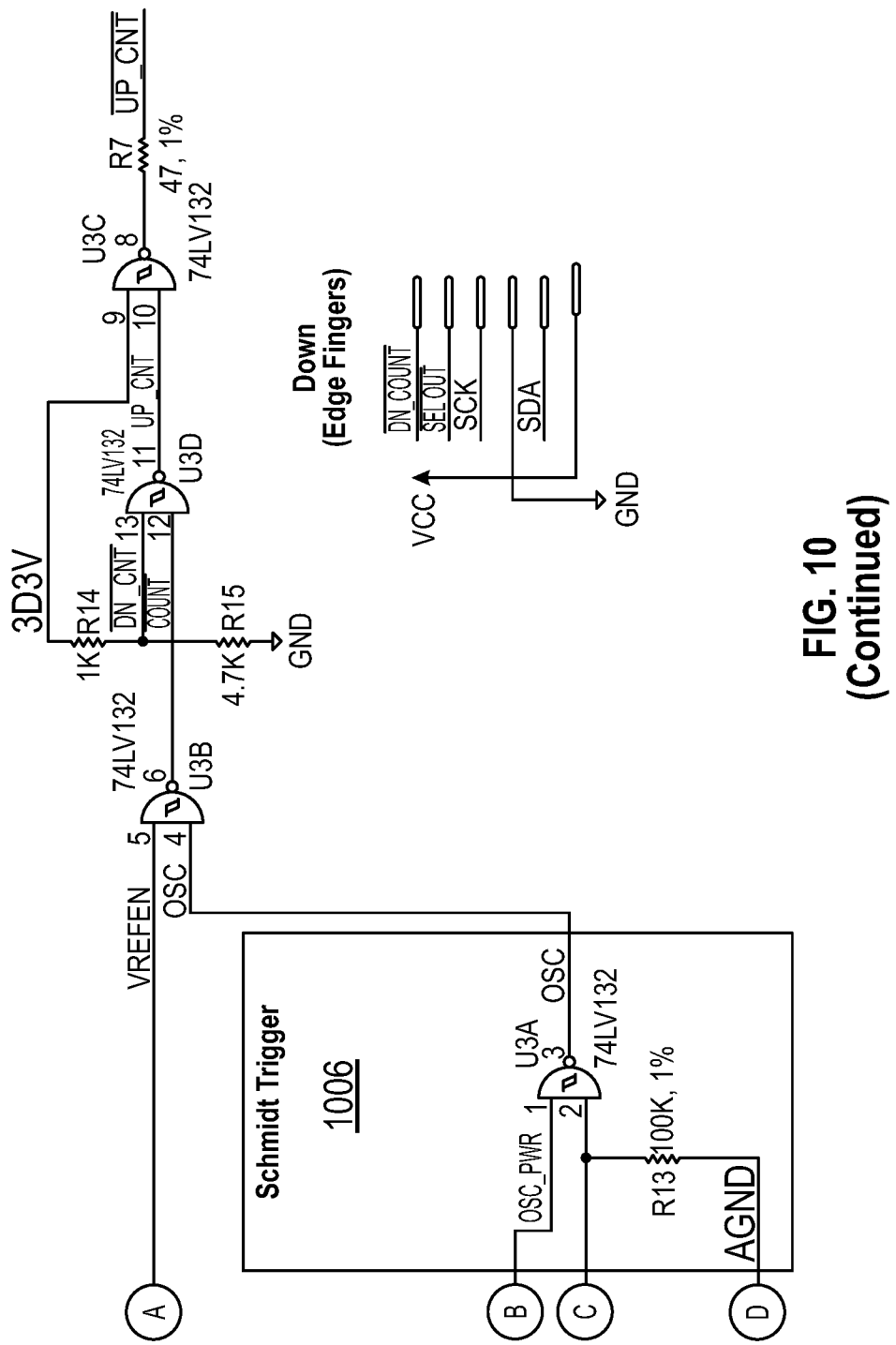

FIG. 10 is a schematic diagram of an example master element 1000 (such as the master element 702 of FIG. 7). The master element 1000 can include a low noise oscillator power element 1002, an oscillator 1004, a Schmitt trigger 1006, as well as a pi filter 1008, a thermistor 1010, and a processor 1012. The low noise oscillator power 1002 can provide a regulated amount of power to the oscillator 1004. The oscillator 1004 can be electrically coupled to an antenna through an antenna connector 1014. The antenna coupled to the master element 1000 through the oscillator 1004 can include, for example, the antenna 900 of FIG. 9.

In some embodiments, the oscillator 1004 can include a temperature controlled crystal oscillator (TXCO) that provides improved accuracy due to any combination of improved reference frequency, better layout, and the use of an antenna without a stub or tail section, as well as a more accurate voltage reference for the oscillator 1004. In contrast with the embodiments of FIGS. 1-6, the master element 1000 does not include a comparator; the oscillator frequency is digitized by a Schmitt trigger.

In operation, the processor 1012 can activate the oscillator 1004 to generate a signal that operates as a clock. The signal is propagated out into the soil surrounding the master element 1000 out to a specified distance using an antenna. The oscillator 1004 can operate at 100 MHz an produces a signal that can be sampled as a sin wave to produce a digitized signal using the Schmitt trigger 1006. That is, the Schmitt trigger 1006 digitizes the clock signal of the oscillator 1004. Broadly, the digitized oscillating frequency is directly representative of the moisture in the soil. These digitized signals can be interpreted by the processor 1012 as a moisture level In some embodiments, the pi filter 1008 is used to filter noise. The thermistor 1010 can utilize the voltage through oscillator to calculate a temperature value of the soil surrounding the master element 1000. The processor 1012 can convert the signals generated by the thermistor 1010 to temperature values using a lookup table (or other similar method).

To be sure, the temperature measurements obtained using the thermistor 1010 can be used in combination with the digitized oscillator signals to determine when the soil has been recently watered. To be sure, watering of the soil may result in a temperature drop of the soil depending on the temperature of the water used to irrigate the soil.

Figure 11:
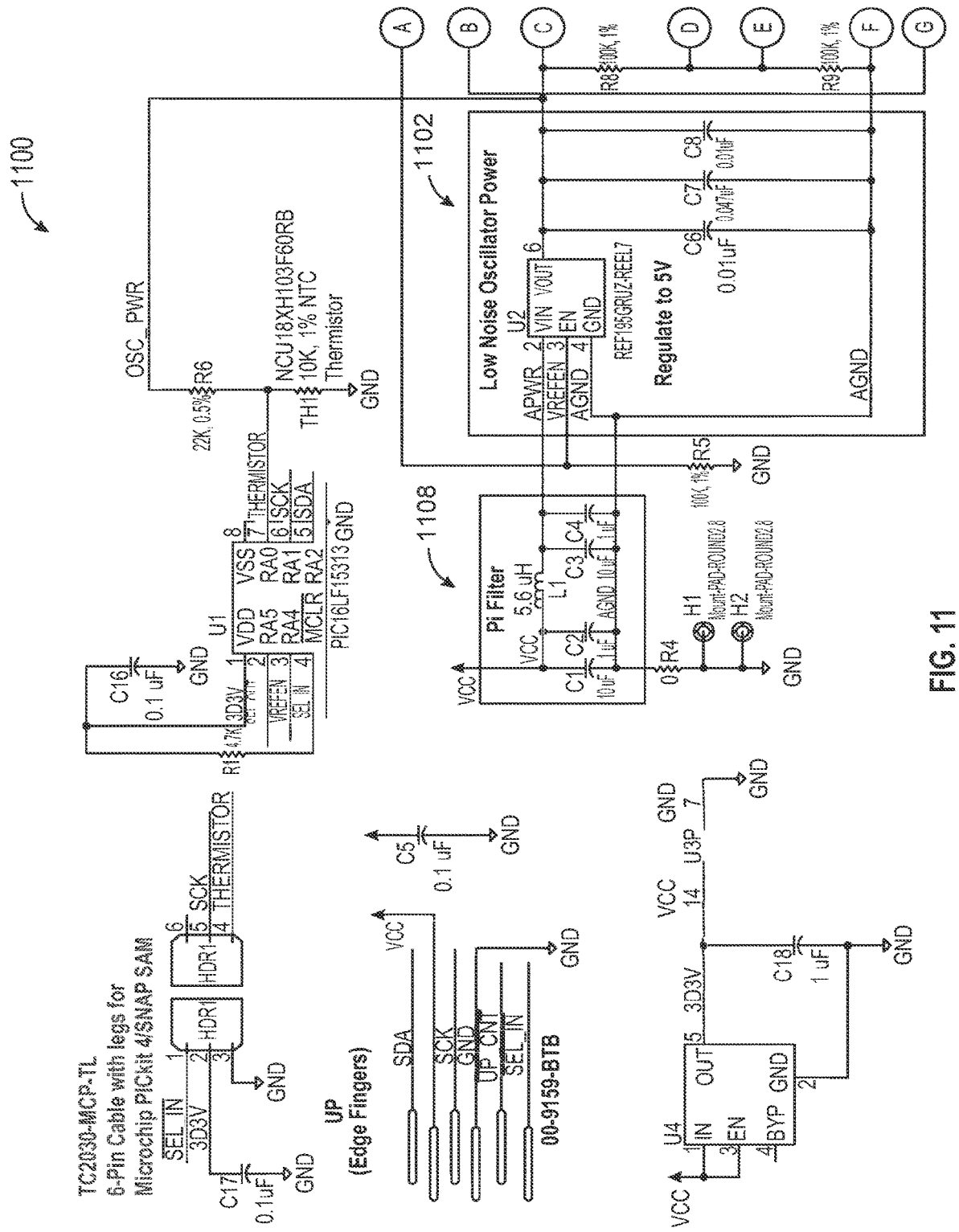
FIG. 11 is a schematic circuit diagram for a slave element of the present disclosure.
Figure 11:
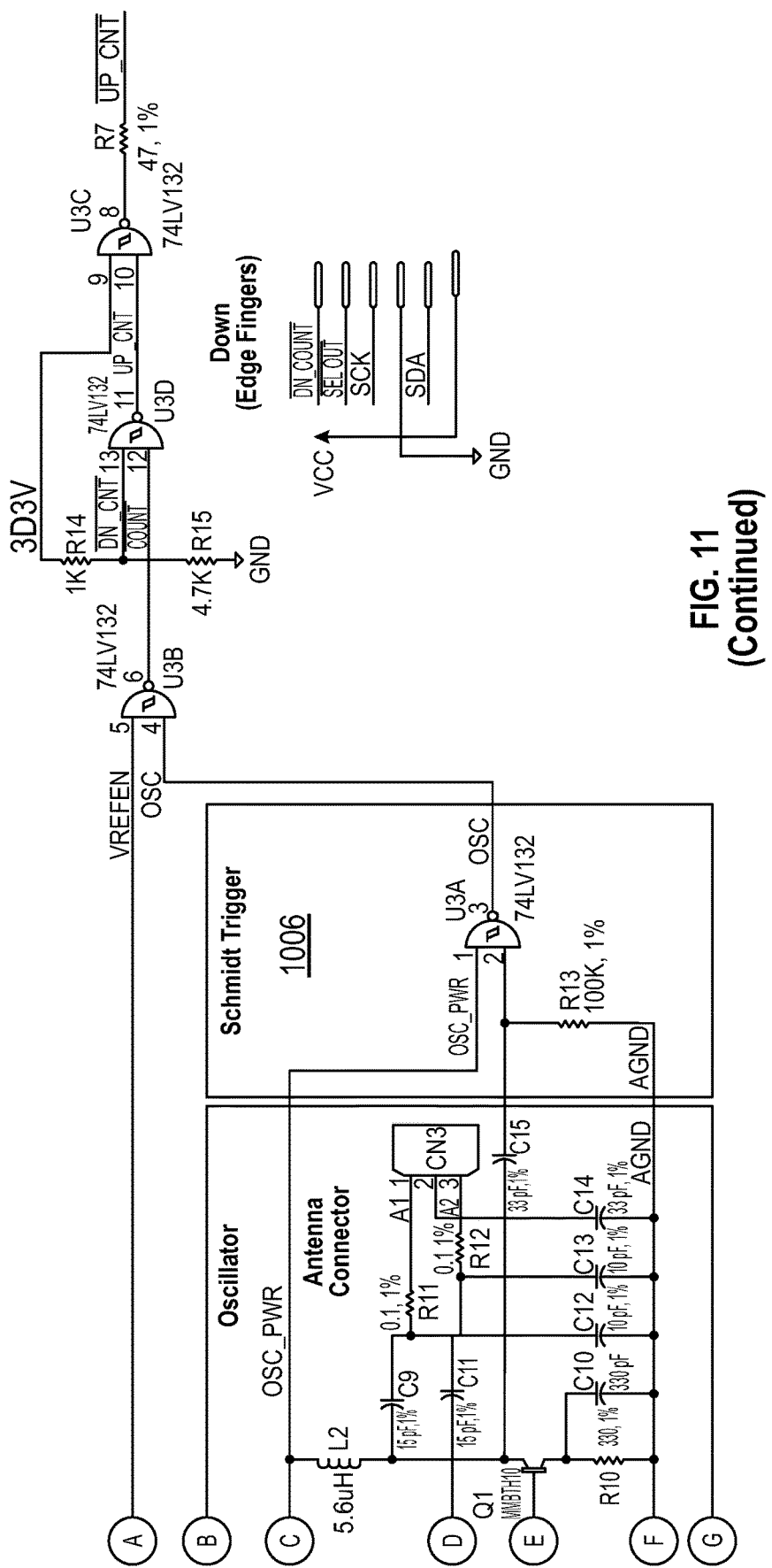

FIG. 11 is a schematic diagram of an example slave element 1100. In contrast with the master element of FIG. 10, the slave element 1100 can include a low noise oscillator power element 1102, an oscillator, a Schmitt trigger, as well as a pi filter 1108. The slave element 1100 does not require a dedicated processor or a thermistor element. The components of the slave element 1100 provide the same functions as described above with respect to the master element 1000. Any number of slave elements can be arranged in series below a master element.

Each slave element can be configured to obtain soil sample signals as disclosed above. A master element can automatically detect and assign a number/address to each slave element in the array. Because the slave elements are of a known size, the master can know what depth each element is in the soil.

The master element can activate any of the slave elements to obtain soil moisture measurements. As a slave element receives signals from the soil, these signals can be buffered and transmitted up to the master. For example, if two slave elements are present, the lowermost slave element can buffer and transmit its soil signals up to the slave element above. The first slave element can then buffer the signals from the lowermost slave element and transmit these signals up to the master element. The first slave element can also buffer and transmit its signals upward to the master element.

Figure 12:
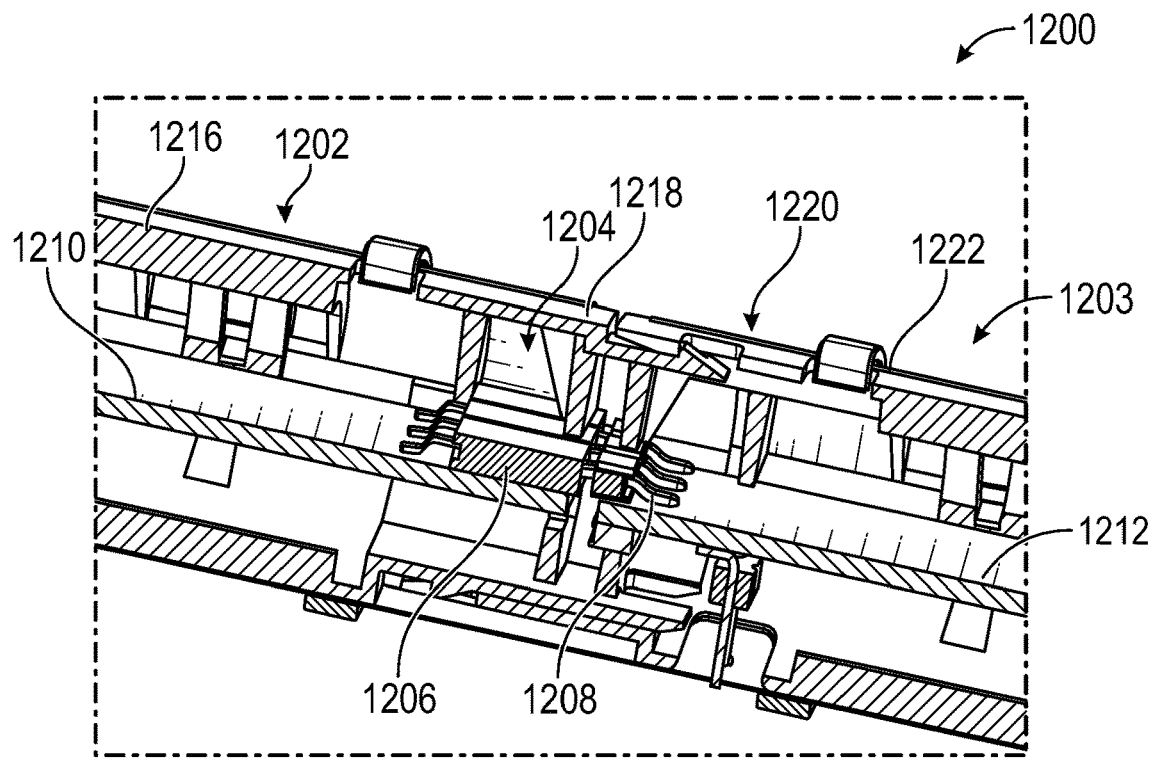
FIGS. 12 and 13 collectively depict conductive mechanical interfaces for coupling elements of the present disclosure.
Figure 13:
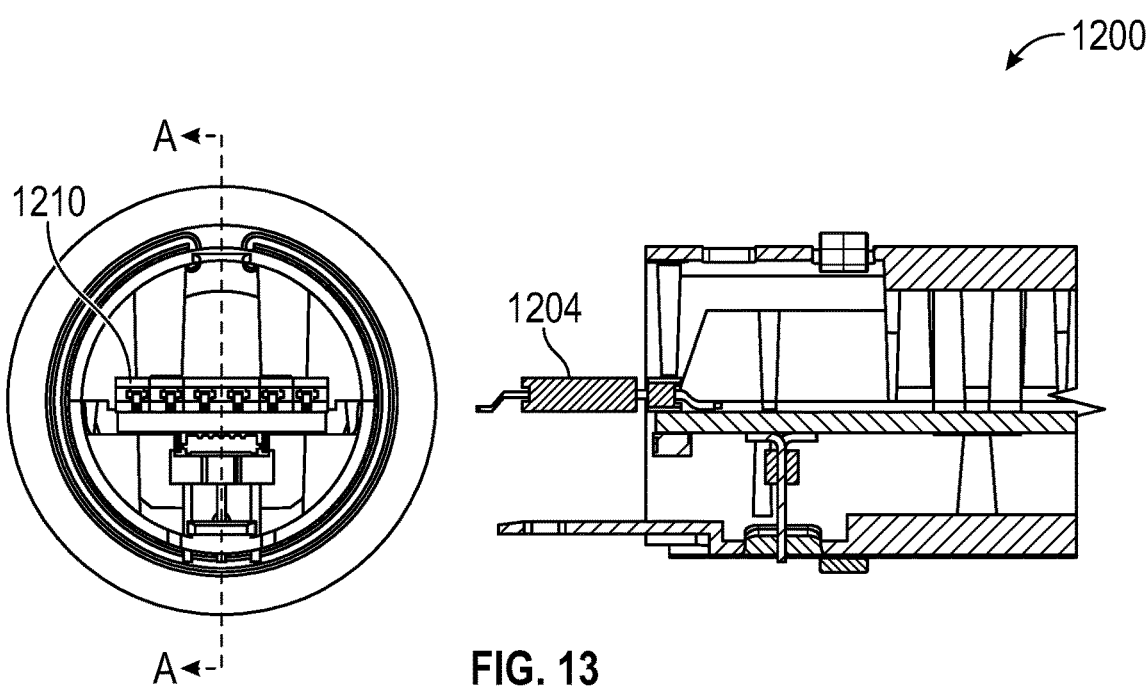

As noted above, the element arrays disclosed herein can be connected in a modular fashion. FIGS. 12 and 13 collectively illustrate conductive mechanical interfaces between two elements in an array 1200. These conductive mechanical interfaces can be disposed on the ends of master or slave elements. In one example, a first element 1202 has a series of conductive mechanical interfaces 1204 disposed on a terminal end.

Each of the conductive mechanical interfaces 1204 includes insulators, such as an insulator 1206 that surrounds a conductor 1208. The conductor 1208 spans and electrically couples a first PCB 1210 of the first element 1202 with a second PCB 1212 of the second element 1203.

A housing 1216 of the first element 1202 includes a mechanical latch or other securement element 1218 that cooperates with a catch 1220 fabricated into a housing 1222 of the second element 1203. Another similar latch and catch arrangement can be used on an opposing side of the array, but with the latch being associated with the second element and the catch being associated with the first element. When the first element 1202 and the second element 1203 are connected together, the conductive mechanical interfaces mate, as well as the latches and catches. The conductive mechanical interfaces create an electrical coupling between the two elements and the latches/catches create a mechanical/physical connection between the housings of the two elements.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A device, comprising:
   a master element having:
      a first oscillator circuit for emitting a first inductance frequency and a second inductance frequency, the first oscillator circuit being coupled to a first antenna;
      a CPU (central processing unit) coupled to the first oscillator circuit; and
      an analog bus; and
   a first slave element having:
      a second oscillator circuit for emitting the first inductance frequency and the second inductance frequency, the second oscillator circuit being coupled to a second antenna;
      a CPU (central processing unit) coupled to the second oscillator circuit;

an upstream analog bus coupled to the analog bus of the master element; and a downstream analog bus configured to couple with another downstream slave element.

2. The device according to claim 1, wherein the master element further comprises a temperature sensor.

3. The device according to claim 1, wherein the master element further comprises an electro-conductivity sensor that obtains electro-conductivity measurements of soil that are used to determine or infer fertilizer content in the soil.

4. The device according to claim 1, wherein the CPU of the master element and the CPU of the first slave element are each configured to:

obtain a first inductance frequency sample;

obtain a second inductance frequency sample;

obtain a temperature reading from a temperature sensor; and transmit the first inductance frequency sample, the second inductance frequency sample, and the temperature reading to a service provider.

5. The device according to claim 1, wherein the CPU of the master element is configured to:

wake up based on a received wake up signal; and output a first pulse to the first slave element to determine when the first slave element is present.

6. The device according to claim 5, wherein the CPU of the master element is configured to receive a response pulse from the first slave element, wherein the response pulse has a period that is longer than a period of the first pulse.

7. The device according to claim 6, wherein the CPU of the master element is configured to transmit a unique identifier to the first slave element after receiving the response pulse.

8. The device according to claim 7, wherein the CPU of the master element is configured to receive a signal from a last downstream slave element that indicates that no other downstream slave elements have been detected.

9. The device according to claim 7, wherein the CPU of the master element is configured to address a command to the first slave element, the command having the unique identifier for the first slave element and instructions to obtain a soil moisture reading.

10. The device according to claim 1, wherein the master element is stacked vertically on top of the first slave element.

11. The device according to claim 1, wherein the device is buried in an area of soil.

12. A method, comprising:

waking a master element of a soil analysis device;

outputting a first signal or pulse to a first downstream slave element connected to the master element through an analog bus;

receiving a first response signal or pulse from the first downstream slave element;

transmitting a unique identifier downstream to the first downstream slave element;

outputting, by the first downstream slave element, a second signal or pulse to a second downstream slave element connected to the first downstream slave element through a downstream analog bus;

receiving a second response signal or pulse from the second downstream slave element;

transmitting a unique identifier downstream to the second downstream slave element;

transmitting, by the master element, a command to either of the first downstream slave element or the second downstream slave element; and receiving a moisture signal and a temperature signal from either of the first downstream slave element or the second downstream slave element based on the command.

13. The method according to claim 12, further comprising receiving a signal from a last downstream slave element that no additional downstream slave elements have been found, wherein the signal is transmitted upstream to the master element.

14. The method according to claim 12, wherein the first response signal has a period that is longer than a period of the first signal.

15. The method according to claim 14, further comprising:

obtaining electro-conductivity measurements of soil; and transmitting the electro-conductivity measurements to a service provider over a network.

16. The method according to claim 12, further comprising determining or inferring fertilizer content in soil using machine learning by a service provider.

17. The method according to claim 12, further comprising:

obtaining a first inductance frequency sample;

obtaining a second inductance frequency sample;

obtaining a temperature reading from a temperature sensor; and transmitting the first inductance frequency sample, the second inductance frequency sample, and the temperature reading to a service provider.

18. The method according to claim 17, wherein the first inductance frequency sample, the second inductance frequency sample, and the temperature reading are obtained from each of the master element, the first downstream slave element, and the second downstream slave element.

19. The method according to claim 12, further comprising burying the soil analysis device below ground.

20. The method according to claim 12, wherein the first pulse has a period that is longer than a period of the first pulse.

* * * * *